United States Patent
Shiba et al.

(10) Patent No.: US 10,877,016 B2
(45) Date of Patent: Dec. 29, 2020

(54) FUEL OIL IDENTIFICATION SENSOR EQUIPPED WITH RECEPTOR LAYER COMPOSED OF HYDROCARBON-GROUP-MODIFIED PARTICLES, AND FUEL OIL IDENTIFICATION METHOD

(71) Applicant: NATIONAL INSTITUTE FOR MATERIALS SCIENCE, Ibaraki (JP)

(72) Inventors: Kota Shiba, Ibaraki (JP); Genki Yoshikawa, Ibaraki (JP); Gaku Imamura, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 198 days.

(21) Appl. No.: 15/781,924

(22) PCT Filed: Nov. 14, 2016

(86) PCT No.: PCT/JP2016/083689
§ 371 (c)(1),
(2) Date: Jun. 6, 2018

(87) PCT Pub. No.: WO2017/098862
PCT Pub. Date: Jun. 15, 2017

(65) Prior Publication Data
US 2018/0356388 A1   Dec. 13, 2018

(30) Foreign Application Priority Data
Dec. 8, 2015 (JP) ................................. 2015-239115

(51) Int. Cl.
*G01N 33/22* (2006.01)
*C10L 1/02* (2006.01)
(Continued)

(52) U.S. Cl.
CPC ............... *G01N 33/22* (2013.01); *C10L 1/02* (2013.01); *C10L 1/04* (2013.01); *G01L 1/18* (2013.01);
(Continued)

(58) Field of Classification Search
CPC ...... G01N 33/22; G01N 33/0047; G01N 5/02; G01N 21/553; G01L 1/18; C10L 1/04; C10L 1/02
See application file for complete search history.

(56) References Cited

U.S. PATENT DOCUMENTS

2002/0141901 A1   10/2002  Lewis et al.
2003/0109056 A1   6/2003   Vossmeyer et al.
(Continued)

FOREIGN PATENT DOCUMENTS

CN  1402000      3/2003
JP  2003-506714  2/2003
(Continued)

OTHER PUBLICATIONS

"Highly sensitive alkane odour sensors based on functionalized gold nanoparticles" by AlQahtani et al. (Year: 2011).*
(Continued)

*Primary Examiner* — Xin Y Zhong
(74) *Attorney, Agent, or Firm* — Wenderoth, Lind & Ponack, L.L.P.

(57) ABSTRACT

Provided is a sensor which enables detection/identification of various types of fuels for automobiles by using simple devices. According to the present invention, high-octane gas, regular gas, diesel oil, heating oil, gasoline laced with heating oil, and the like can be clearly identified without using a large-scale analysis such as gas chromatography or mass spectroscopy by using a sensor having a structure in which a surface of a sensor body which detects a surface stress or the like is coated with particles modified with a hydrocarbon group such as an alkyl group.

18 Claims, 25 Drawing Sheets

(51) Int. Cl.
   C10L 1/04    (2006.01)
   G01N 5/02    (2006.01)
   G01N 33/00   (2006.01)
   G01L 1/18    (2006.01)
   G01N 21/552  (2014.01)

(52) U.S. Cl.
   CPC .......... G01N 5/02 (2013.01); G01N 33/0047 (2013.01); *G01N 21/553* (2013.01)

(56) References Cited

U.S. PATENT DOCUMENTS

| 2013/0133433 A1 | 5/2013 | Yoshikawa et al. |
| 2018/0003604 A1 | 1/2018 | Shiba et al. |

FOREIGN PATENT DOCUMENTS

| JP | 2004-117325 | 4/2004 |
| WO | 00/22130 | 4/2000 |
| WO | 2009/113314 | 9/2009 |
| WO | 2011/148774 | 12/2011 |
| WO | 2016/121155 | 8/2016 |

OTHER PUBLICATIONS

"Gold-nanoparticle/organic linker films: self-assembly, electronic and structural characterisation, composition and vapour sensitivity" by Joseph et al. (Year: 2003).*

"A hybrid chemiresistive sensor system for the detection of organic vapors" by Im et al. (Year: 2011).*

"A Room Temperature Polymer-Coated Piezoresistive Silicon Bridge Gasoline Vapor Sensor". By Guo et al. (Year: 2012).*

International Search Report dated Jan. 24, 2017 in International Application No. PCT/JP2016/083689.

Huihui Guo, Xiangdong Chen, and Yao Yao, "A Room Temperature polymer-Coated Piezoresistive Silicon Bridge Gasoline Vapor Sensor," IEEE Sensors Journal, vol. 12, No. 5, 926-929, (2012).

K. Shiba, T. Sugiyama, T. Takei, and G. Yoshikawa, "Controlled growth of silica-titania hybrid functional nanoparticles through a multistep microfluidic approach," Chem. Commun. 51, 15854-15857 (2015).

Notification of Reasons for Refusal dated May 14, 2019 in Japanese Patent Application No. 2017-554985, with Machine Translation.

Extended European Search Report dated Jul. 24, 2019 in European Patent Application No. 16872762.6.

Hadi AlQahtani et al., "Highly sensitive alkane odour sensors based on functionalised gold nanoparticles", Sensors and Actuators B, 2011, vol. 160, No. 1, pp. 399-404.

Jisun Im et al., "A hybrid chemiresistive sensor system for the detection of organic vapors", Sensors and Actuators B, 2011, vol. 156, No. 2, pp. 715-722.

Yvonne Joseph et al., "Gold-nanoparticle/organic linker films: self-assembly, electronic and structural characterisation, composition and vapour sensitivity", Faraday Discussions, 2003 (web publication), vol. 125, pp. 77-97.

Office Action dated Mar. 24, 2020 in corresponding Chinese Patent Application No. 201680071174.4, with English translation.

Lukowiak et al., "Application of a titania thin film for the discrimination between diesel fuel and heating oil", Thin Solid Films, vol. 515, 2007, pp. 7005-7010.

* cited by examiner

FUEL OIL IDENTIFICATION SENSOR EQUIPPED WITH RECEPTOR LAYER COMPOSED OF HYDROCARBON-GROUP-MODIFIED PARTICLES, AND FUEL OIL IDENTIFICATION METHOD

TECHNICAL FIELD

The present invention relates to a sensor coated with particles which are modified with a hydrocarbon group such as an alkyl group or an aryl group, and specifically relates to a sensor which enables identification among various fuel oils such as a fuel oil used in an internal combustion engine. The present invention further relates to a fuel oil identification method using the sensor.

BACKGROUND ART

Identification among mixtures of gases including a plurality of components is a key issue in various applications from medical care to a variety of industries. As an example, identification among fuel oils has been developed since it is a technique relating to various industries such as an automobile industry concerning specification of gasoline diluted with impurities. Many of the conventional techniques include qualitative analysis of the total components by gas chromatography and quantitative analysis by a mass spectrometer. In such methods, identification cannot be conducted conveniently because the methods require large and expensive dedicated equipment. To address this issue, identification techniques using a small sensor have been developed. The identification using a sensor employs a pattern recognition technique. That is, the surfaces of a plurality of sensors are respectively coated with receptor materials with different properties and a "sensor array" in which those sensors are arranged in an array is used for the measurement to obtain different responses from the respective sensors so as to conduct the pattern recognition. This technique would be able to be applied to various mixed gases, and could be one of the effective approaches for the identification. This technique would, however, require to prepare a relatively large number of materials with different properties and to coat the surfaces of the sensors with them, and thus it would not be easy to optimize the coating conditions for each material. Further, as in the case of substances like fuel oils such as regular gasoline (hereinafter, sometimes abbreviated to "regular gas") or high-octane gasoline (hereinafter, sometimes abbreviated to "high-octane" or "high-octane gas") in which their main components are similar and ratios among them are slightly different, most of the sensors in the sensor array show similar responses, which might make the identification difficult. Thus, it is required to develop a technique which can achieve highly accurate identification more easily and simply.

Non Patent Literature 1 discloses a sensor in which a surface of a silicon substrate is coated with silicone rubber, and a silicone rubber membrane is swelled by absorbing gasoline vapor to detect changes in surface stress applied on the silicon substrate. However, such type of sensor has limitation in application because silicone rubber slowly absorbs and releases gasoline vapor, and thus response speed is slow. Further, the literature specifically discloses detection of gasoline, and provides no description of identification with respect to multiple types of fuel oils.

SUMMARY OF INVENTION

Technical Problem

An object of the present invention is to provide a sensor which enables highly accurate identification of fuel oils by using a material which has high compatibility with a main component of fuel oils as a receptor layer material.

Solution to Problem

According to an aspect of the present invention, a fuel oil identification sensor with the following features is provided; a sensor body configured to detect changes in a physical parameter; and a receptor layer including particles modified with a hydrocarbon group and having a particle size of 1 mm or less, wherein the receptor layer coats a surface of the sensor body.

Here, the physical parameter detected by the sensor body may be at least one selected from the group consisting of a surface stress, a stress, a force, surface tension, a pressure, a mass, elasticity, a Young's modulus, a Poisson's ratio, a resonance frequency, a frequency, a volume, a thickness, a viscosity, a density, a magnetic force, a magnetic charge, a magnetic field, a magnetic flux, a magnetic flux density, an electric resistance, a quantity of electricity, a dielectric constant, an electric power, an electric field, an electric charge, an electrical current, an electric voltage, an electric potential, mobility, electrostatic energy, a capacitance, an inductance, a reactance, a susceptance, an admittance, an impedance, a conductance, a plasmon, a refractive index, luminous intensity, and a temperature.

Further, the particles may be nanoparticles having a particle size of 100 nm or less.

Further, the particles may include: zeolite; Metal-Organic Frameworks; a hybrid of an oxide and/or a metal, and various surfactants; a porous material; graphene; an alkali silicate or a titanate such as a clay mineral; and a low-dimensional compound including a transition metal oxoate.

Further, the receptor layer may further include a matrix material other than the particles.

Further, the sensor body may be selected from the group consisting of a surface stress sensor, a sensor utilizing an oscillator, and a sensor utilizing surface plasmon resonance.

Further, the hydrocarbon group may be an alkyl group or an aryl group.

Further, the alkyl group may be an alkyl group having 1 to 30 carbon atoms.

Further, the alkyl group may be a dodecyl group or an octadecyl group.

Further, the fuel oil may be a fuel oil selected from the group consisting of regular gasoline; high-octane gasoline; diesel oil; heating oil; a mixture of regular gasoline or high-octane gasoline, and an alcohol; heavy oil A; a mixture of heavy oil A and heating oil; and a mixture of at least one of heavy oil A and heating oil, and diesel oil.

According to another aspect of the present invention, a fuel oil identification method with the following features is provided; supplying vapor of an analyte to any of the fuel oil identification sensors; and identifying the analyte on the basis of an output of the fuel oil identification sensor.

Here, a mixture of the vapor of the analyte and another gas may be supplied to the fuel oil identification sensor.

Further, the other gas may be a gas or a mixture of a plurality of gases selected from the group consisting of nitrogen, air, argon, and helium.

Further, the vapor of the analyte may be generated without performing heating or cooling.

Further, the vapor of the analyte may be generated at room temperature.

Further, the vapor of the analyte may be supplied to different types of fuel oil identification sensors; and the analyte may be identified on the basis of an output obtained from each of the fuel oil identification sensors.

Further, vapors of a plurality of analytes may be switched in sequence for delivery to the fuel oil identification sensor Cleaning of the fuel oil identification sensor may not be performed for at least one cycle of the switching for the delivery.

Further, identification of the analyte may be performed by further information processing of the output of the fuel oil identification sensor.

Here, the information processing may be based on at least one analytical method selected from principal component analysis, a neural network, deep learning, a support vector machine, random forest, a decision tree, regression analysis, and big data analysis.

Advantageous Effects of Invention

According to the present invention, use of hydrocarbon-group-modified particles as a receptor layer enables identification of fuel oils by a single sensor, which has been difficult by conventional identification sensors. Accordingly, situations requiring multiple sensors, such as a conventional sensor array, to which different receptor materials are coated are reduced, resulting in significant simplification of factors in a sensor production step, a sensor system, and data analysis. As described below, the present invention does not, of course, exclude use of multiple sensors such as a sensor array, and it is of course possible to apply a form of the sensor array or the like, as required.

DESCRIPTION OF EMBODIMENTS

Figure 1:
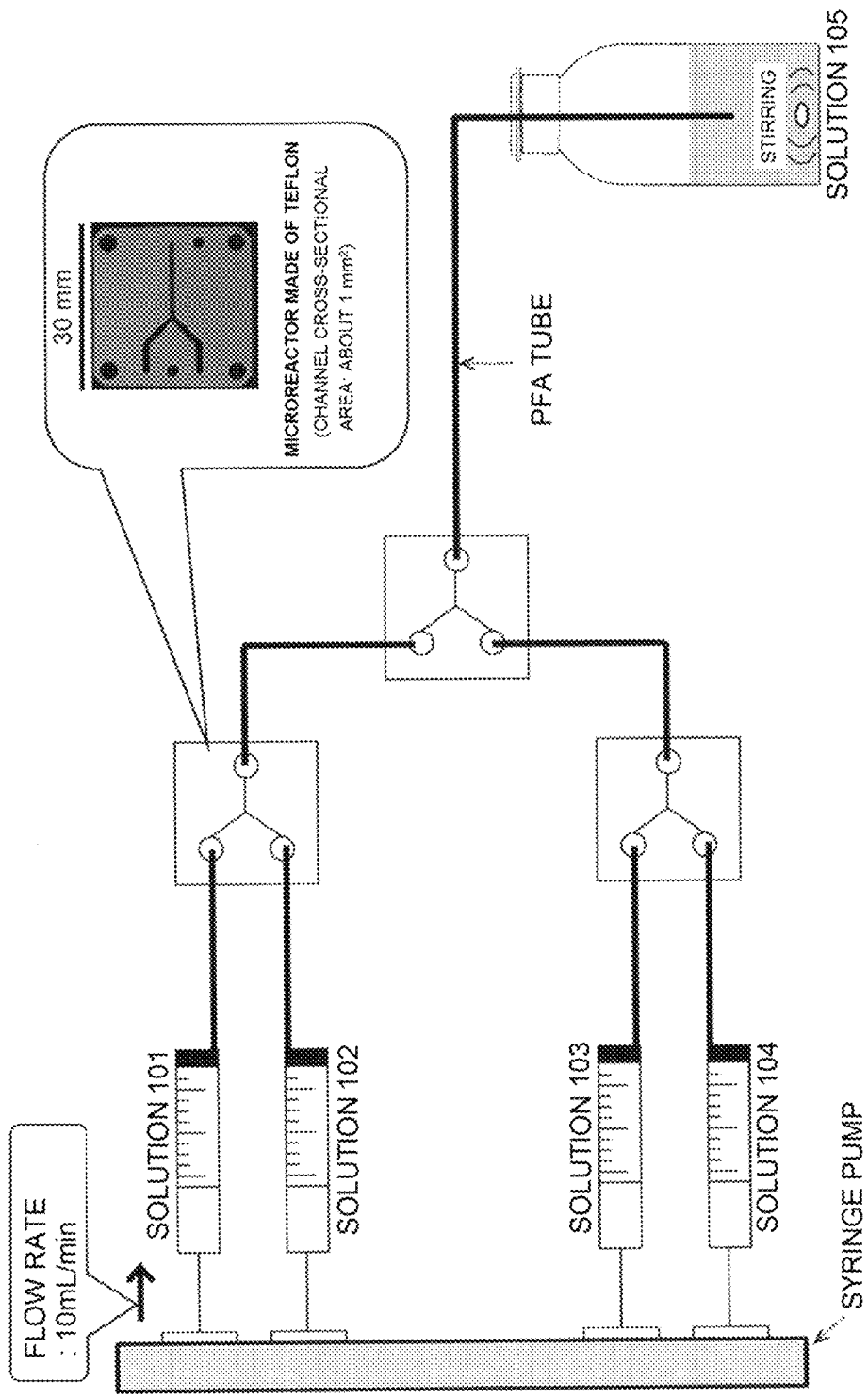
FIG. 1 is a conceptual diagram showing an example of a configuration of devices utilized for synthesis of octadecyl group-modified nanoparticles.

According to one aspect of the present invention, a sensor with following features is provided; a sensor coated with an alkyl group modified particles receptor layer constituted by direct deposition of hydrocarbon-group-modified particles on a sensor body which detects one or a combination of various physical parameters selected from a surface stress, a stress, a force, surface tension, a pressure, a mass, elasticity, a Young's modulus, a Poisson's ratio, a resonance frequency, a frequency, a volume, a thickness, a viscosity, a density, a magnetic force, a magnetic charge, a magnetic field, a magnetic flux, a magnetic flux density, an electric resistance, a quantity of electricity, a dielectric constant, electric power, an electric field, an electric charge, an electrical current, an electric voltage, an electric potential, mobility, electrostatic energy, a capacitance, an inductance, a reactance, a susceptance, an admittance, an impedance, a conductance, a plasmon, a refractive index, luminous intensity, and a temperature, and various other physical parameters.

Here, the hydrocarbon groups which modify the particles include various types of hydrocarbon groups such as an alkyl group and an aryl group. When the hydrocarbon group is an alkyl group, a methyl group having one carbon atom to a triacontyl group having 30 carbon atoms can be preferably used. Although such an alkyl group exemplified in examples consists of a straight alkyl chain, the alkyl group is not limited to a straight alkyl chain, and an alkyl group having a side chain can also be used. Further, an unsaturated hydrocarbon with a chain structure can be used as well as an alkyl group. More generally, the hydrocarbon groups can be aromatic hydrocarbon groups and other cyclic hydrocarbon groups.

Note that binders, which improve a property of forming particle aggregation or adhering to a sensor body, or other constituents can be added in addition to particles which bind to an analyte. For example, a matrix material for regulating adhesion to a sensor body or disperse/aggregation of particles can be used, for example, a polymer or the like can further be added to particles. It is also possible to increase compatibility with particles by coating of a self-assembled monolayer, that is, it is possible to enhance adhesion between a nanoparticle and a surface of a sensor body through a self-assembled monolayer.

The sensor detects changes in physical parameters produced in the receptor layer due to adsorption of an analyte in a fuel oil on the receptor layer by a sensor body. Accordingly, structures, operations, and the like of a sensor body which can be used in the present invention are not specifically limited so long as the sensor body can detect changes of the receptor layer produced by adsorption of a substance to be detected in a fuel oil on a hydrocarbon-group-modified particles receptor layer such as an alkyl group coated onto the surface of the sensor body. For example, when a surface stress sensor is used, by adsorption of a substance to be detected in a fuel oil by a hydrocarbon-group-modified particles receptor layer coated onto the surface of the surface stress sensor, the surface stress sensor detects changes of a stress produced in the receptor layer and outputs a signal.

In the hydrocarbon-group-modified particles receptor layer of the present invention, shapes of a particle on which a hydrocarbon group is fixed can be isotropic or anisotropic. Materials constituting the particle may include an elementary substance such as a metal, a compound such as an oxide or a sulfide, a polymer, an inorganic-organic hybrid, or a bio-related material such as a protein. Specifically, the materials which can be used include, but are not limited to, zeolite, Metal-Organic Frameworks (MOF), a hybrid of an oxide and/or a metal and various surfactants, a porous material, graphene, an alkali silicate or titanate such as a clay mineral, and a low-dimensional compound including a transition metal oxoate.

Further, a size of the particle is preferably 1 mm or less because adhesive force is increased due to greater influence of van der Waals interaction than that of gravity or the like. The particle size is more preferably 100 µm or less, even more preferably 1 µm or less, still more preferably 100 nm or less. In any case, the particle size is not limited so long as the particle adheres to a surface of a sensor body by a kind of interaction. In one aspect, however, it is important that the particle is not easily detached from the surface of the sensor body.

Any coupling material having a hydrocarbon group in the molecular structure, such as silane, phosphonic acid, thiol, amines, or a surfactant can be used for fixing a hydrocarbon group.

Further, hydrocarbon-group-modified particles synthesized by any method can be used. Specifically, the method includes, but is not specifically limited to, a precipitation reaction in a homogeneous solution, a reaction in a pseudo-homogeneous system utilizing an emulsion, a gaseous phase reaction utilizing spray drying or pyrolysis, or a solid phase reaction such as ball milling.

Examples of the sensor body coated with a hydrocarbon-group-modified particles receptor layer include various types of surface stress sensors as described in Patent Literature 1, for example. However, a shape, a material, a size, or the like of the sensor body is not specifically limited, and any object can be used. Preferred examples include, for example, a slice-like component which is supported at one or multiple portions. In addition, sensor bodies having various forms, such as slice-like objects supported at two or more portions, for example, a double-supported beam, membranes, and the like can be adopted.

Further, for example, an oscillator such as QCM or a cantilever, or a sensor utilizing surface plasmon resonance (Surface Plasmon Resonance, SPR), in addition to a surface stress sensor, can be coated with a granular material receptor and can achieve a similar effect as described above.

Methods for coating a surface of a sensor with a hydrocarbon-group-modified particles receptor include, but are not specifically limited to, dip coating, spray coating, spin coating, casting, and a coating using a doctor blade.

Note that, as used in the specification and claims in the present invention, "a fuel oil" refers to a hydrocarbon-based oil whose main component is a specific distillate of crude oil, which is used as fuel for an internal combustion engine or various fuels such as heating oil, or an oil which is about equal in properties to the specific distillate, such as a synthetic petroleum derived from coal. However, fuel oils of the present invention include not only a hydrocarbon such as a distillate of crude oil, but also the hydrocarbon to which various additives are added. For example, commercially available gasoline or diesel oil for automobiles contains various additives for the purpose of, for example, improving its properties. Further, plant-derived alcohol, which is not included in an amount of carbon dioxide emissions under a treaty when it is burned, is added to some gasoline, and fuel oils of the present invention also include such a fuel oil containing an ingredient which is not derived from crude oil. Further, as a fuel for an internal combustion engine, for example, for a fuel for automobiles, only fuels which comply with industrial standards or which are permitted by laws such as the tax law can be used. However, illegal gasoline containing heating oil, or oil produced by illegally treating heavy oil A or heating oil or adulterated diesel oil produced by adding such oil produced by illegally treating heavy oil A or heating oil to diesel oil is sometimes distributed and used stealthily. Thus, whether fuel oils comply with a standard/law or not, the present invention encompasses all of the fuel oils circulated and used as various fuel oils.

Further, in examples described below, nitrogen was used as a carrier gas for sending sample vapor to a sensor chamber, or used to accelerate desorption of an adsorbed sample. However, it is of course not limited to nitrogen, and any gas including air, nitrogen, argon, helium, and a mixed gas containing two or more of these gases may be used. Although carrier gases are described above, sample vapor can be sent to a sensor together with a gas present in vacant spaces such as upper space of a container containing the sample without supplying any gas from outside as a carrier gas for sending the sample vapor to the sensor. Further, needless to say, vapor of a sample can be solely sent to a sensor without mixing with other gases. Alternatively, when a sensor is placed in a position where vapor from a sample can naturally arrive at by convection, diffusion or the like, for example, when a sensor is placed in a container (e.g., upper space of the container) such as a fuel tank containing the sample, or a sensor is placed in another area close and communicating to the container, even sending of vapor is not required.

Further, in examples, a sensor was cleaned by using nitrogen, then various sample vapors were allowed to flow for the measurements of sensor responses with respect to the samples to identify difference of the responses by principal component analysis. However, the method for measurements and analytical methods are of course not limited to the methods used in examples. For example, for identifying types of gasoline or presence or absence of mixed materials, a possible application method includes allowing one type of sample vapor to flow, and immediately allowing another type of sample vapor to flow without cleaning the sensor by using nitrogen or the like, and then measuring changes of sensor responses at that time. Further, any analytical approaches can be used including a neural network, deep learning, a support vector machine, random forest, a decision tree, and regression analysis, and a specific analytical method which is an application of a big data analysis technology.

A hydrocarbon-group-modified particles receptor of the present invention includes the following characteristics.

(1) A surface of the particle is coated with a hydrocarbon group to achieve compatibility with a hydrocarbon-based compound, which is a main component of a fuel oil.

(2) A type of hydrocarbon compounds which can be detected or identified can be changed by changing structures of hydrocarbon groups which are immobilized on the surface of particles. Further, since materials which can be favorably detected/identified vary depending on immobilized hydrocarbon groups, by using a plurality of types of sensors of the present invention coated with particles modified with different types of hydrocarbon groups and combining outputs of the sensors, it is possible to detect/identify a wider variety of hydrocarbons, fuel oils, and the like.

(3) By using particles as a material of a receptor layer, space (a route) for a hydrocarbon-based compound to reach the inside of the receptor layer can be secured. Specifically, by changing sizes or shapes of stacked hydrocarbon-group-modified particles, sizes of voids formed in the hydrocarbon-group-modified particle can be controlled. The existence of the route communicating to the inside of the receptor layer provides higher responsivity as compared to a receptor layer, such as a conventional polymer layer, in which an analyte arrives at the inside of the receptor layer by mainly diffusion of the analyte from the surface of a membrane into the inside of the receptor layer.

(4) High water resistance is achieved by modification with a hydrophobic hydrocarbon group. For example, measurement can be performed even under high-humidity environments without influence of humidity.

(5) In the following examples, detection was performed by measuring analytes evaporated from a fuel oil at room temperature (about 25° C.), whereas an analyte can of course be evaporated by heating when the analyte was supplied to a sensor of the present invention. Although gasoline is extremely volatile, since diesel oil whose boiling point is defined as about 350° C. or less was also detected in the same manner as gasoline, it was demonstrated that a sensor of the present invention exhibited a high capability to detect/identify fuel oils, which are defined to have a high boiling point, around room temperature. With respect to the description using "room temperature", temperatures in practical application can be a considerably higher temperature or lower temperature than room temperature according to environments in which a fuel oil is placed, for example, when fuels are in a tank placed in a location susceptible to heat of an internal combustion engine or outside air temperature, or fuels are in piping through such a place. Even under such a condition, the present invention can be applicable without performing heating (or cooling) for detection.

EXAMPLES

The present invention is described below in detail with reference to examples. It should be construed that the following examples are of course provided only to facilitate understanding of the present invention, and are not intended to limit the scope of the present invention to the examples in any way. In the following examples, although an example using an alkyl group as a hydrocarbon group is provided, the example is not intended to exclude hydrocarbon groups other than alkyl groups. Since a nanoparticle shown in FIG. 2 was used in the following examples as any of the particles modified with hydrocarbon groups, the particles are referred to as the nanoparticles hereinbelow.

Example 1

Evaluation of properties of a surface stress sensor coated with octadecyl group-modified silica-titania hybrid nanoparticles An example of preparation and measurement of a receptor layer using nanoparticles as described above is demonstrated.

Figure 2:
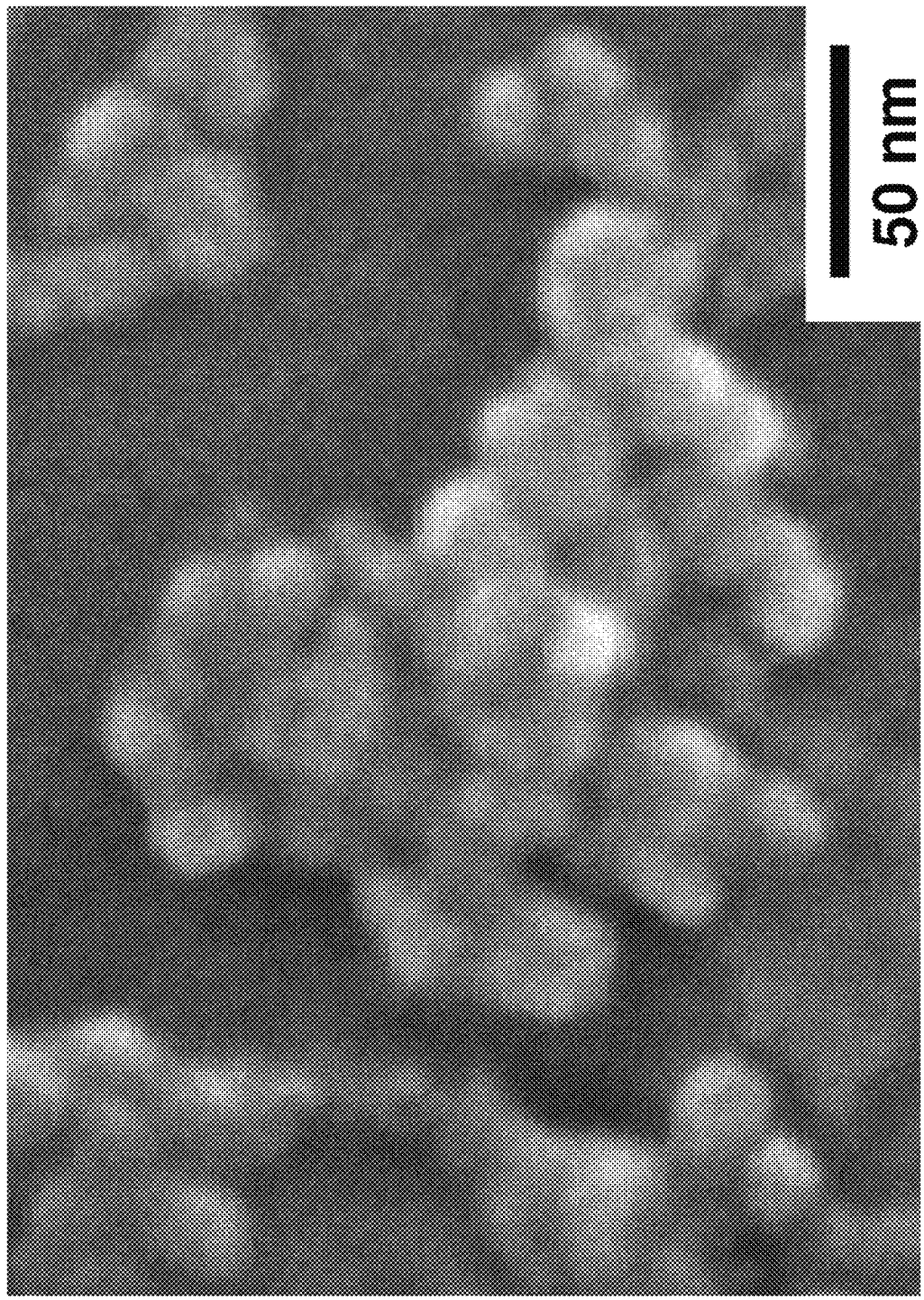
FIG. 2 is a scanning electron microscope (SEM) image of octadecyl group-modified nanoparticles.

The above-mentioned nanoparticles were synthesized on the basis of a method shown in Non Patent Literature 2. Specifically, nanoparticles were synthesized by co-hydrolysis and a condensation polymerization reaction of octadecyl triethoxysilane (ODTES) and titanium tetraisopropoxide (TTIP) in an aqueous ammonia isopropanol (IPA) solution in which octadecylamine (ODA) was dissolved. The above-described synthesis reaction was performed using a microreactor having a micrometer-sized Y-shaped flow path made of Teflon (registered trademark) (FIG. 1). Four precursor solutions were prepared as follows: ODTES/IPA (solution 101), $H_2O$/IPA/ammonia (solution 102), TTIP/IPA (solution 103), and $H_2O$/IPA (solution 104), and volumes of the solution 101 through the solution 104 were equal to one another. Then, the precursor solutions were pumped concurrently at a constant speed using syringe pumps. The solution 101 and the solution 102, and the solution 103 and the solution 104 were respectively mixed in microreactors placed side by side, and then reaction solutions ejected from the two reactors were mixed in another microreactor to make one reaction solution. The reaction solution was added into a precursor solution, which was ODA/$H_2O$/IPA (Solution 105) prepared separately, and the mixture was stirred at a constant speed until the addition was completed. Then, the mixture was aged at room temperature to obtain the above-mentioned nanoparticle dispersion. Images of the nanoparticles observed by SEM are shown in FIG. 2.

The above-described nanoparticle dispersion was centrifuged to remove supernatant, and then IPA was added to the precipitate and the precipitate was redispersed by ultrasonication. The dispersion was centrifuged again, and the above-described step was further repeated twice to eliminate unreacted raw materials and the like. Then, the precipitate was dispersed in IPA, and sprayed on a sensor chip using a spray coater. A piezoresistive surface stress sensor having a membrane-type structure was used as a sensor.

Figure 3:
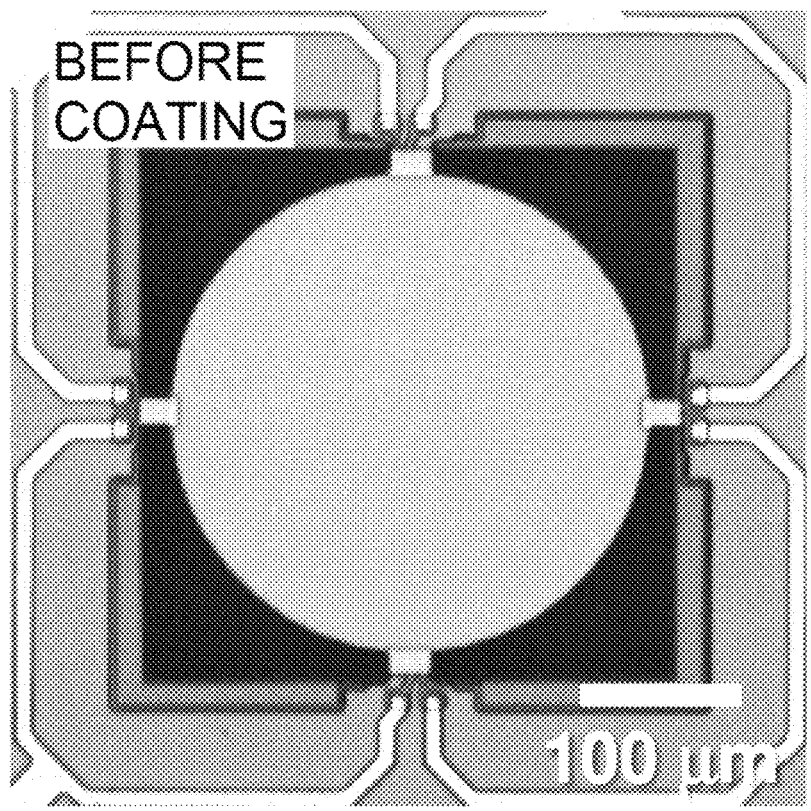
FIG. 3 is an optical microscope image of a membrane-type surface stress sensor before and after coating with octadecyl group-modified nanoparticles.
Figure 3:
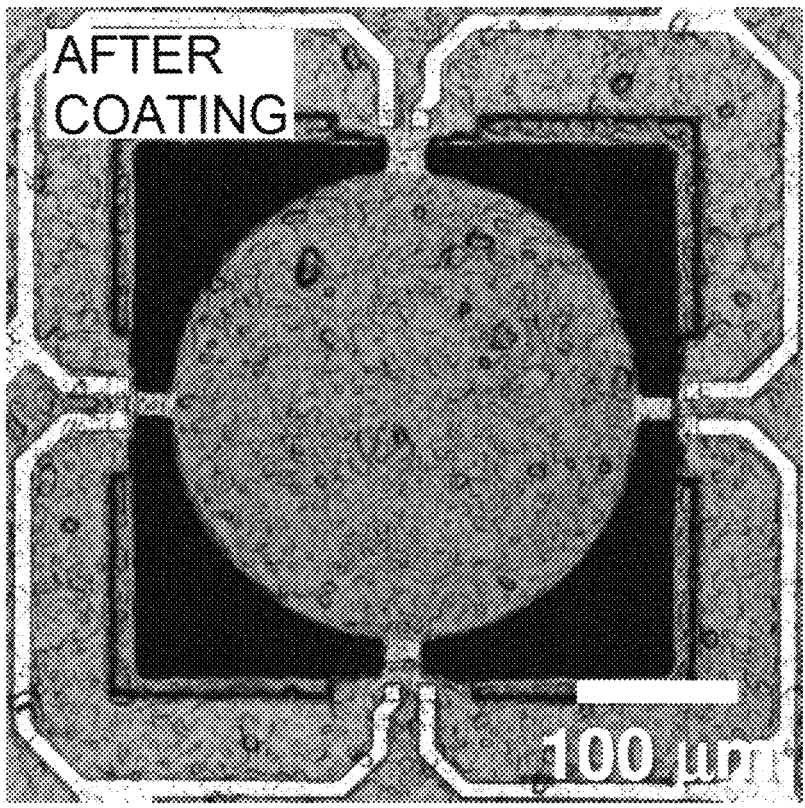

An optical microscope image of the sensor after the nanoparticle coating is shown in FIG. 3. It can be found that the whole membrane surface is coated as compared to that before the coating.

Subsequently, the following 23 types of chemical species were measured. Specifically, the 23 types of species used were water (ultrapure water), formaldehyde (formalin), acetic acid, acetone, methyl ethyl ketone (2-butanone), methanol, ethanol, IPA (isopropanol, 2-propanol), 1-butanol, 1-pentanol, n-hexane, n-heptane, n-octane, n-nonane, n-decane, n-undecane, n-dodecane, benzene, toluene, xylene (mixture of o-, m-, and p-xylene), 1,2-dichlorobenzene, 1,3-dichlorobenzene, and N,N-dimethylformamide. The above-described samples were dispensed in vials, nitrogen was supplied to the vials as a carrier gas at a flow rate of 100 mL/min regulated by a mass flow controller. Thus, the gas containing a certain amount of sample vapor collected in the headspace of the vial was introduced in a tightly-closed chamber in which the sensor was located. Here, the sample vapor was obtained at room temperature. Another mass flow controller was used and operated under the same conditions. However, this mass flow controller was connected with an empty vial, and then connected to the sensor chamber to introduce nitrogen containing no sample vapor. Accordingly, desorption of samples adsorbed on the receptor layer was accelerated to clean the receptor layer. The above-described sample introduction and cleaning were repeated at intervals of 30 seconds, and then results of the measurements were obtained.

Figure 4A:
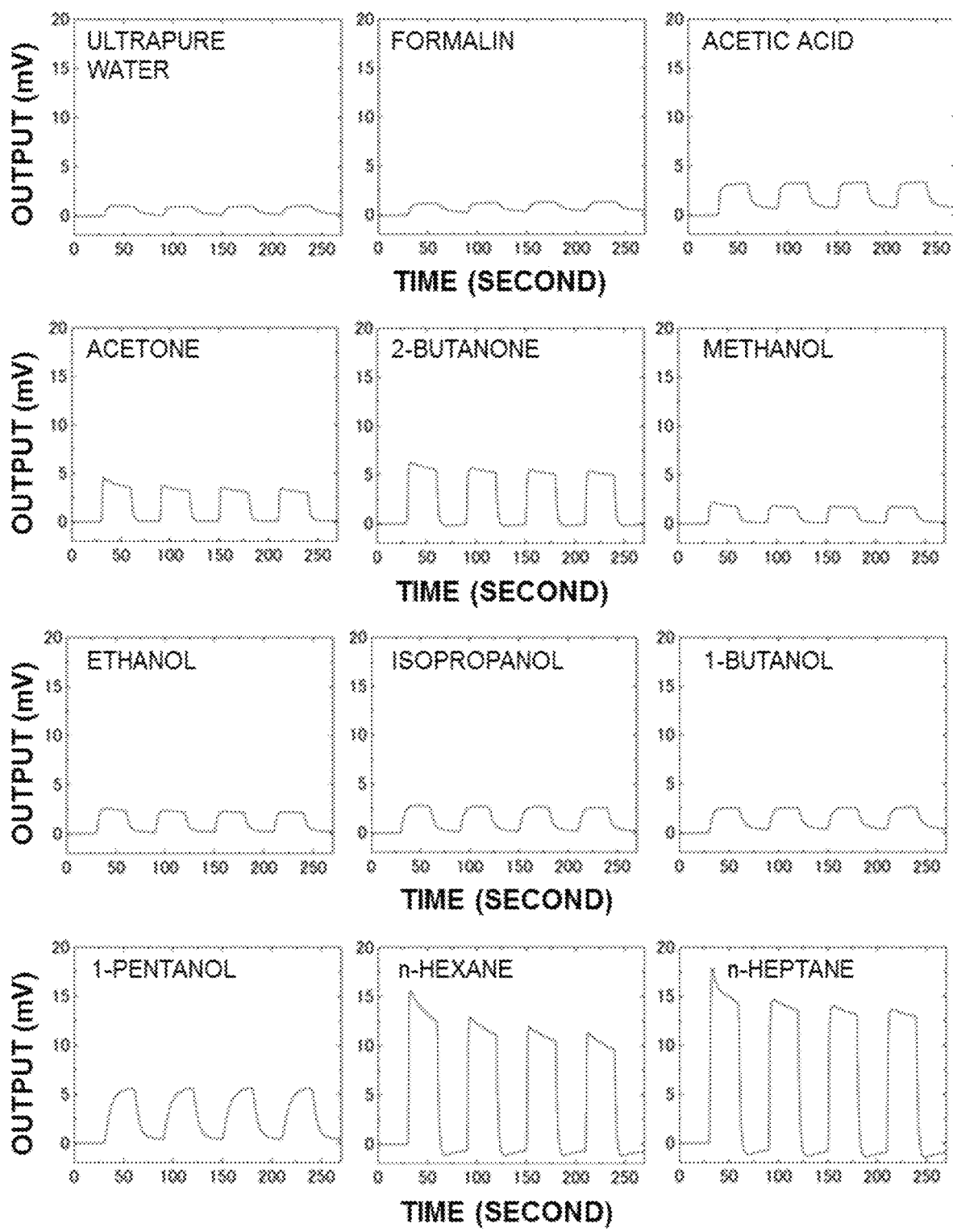
FIG. 4A shows results of measurements of 23 types of compounds by using an octadecyl group-modified nanoparticles-coated membrane-type surface stress sensor (results with respect to 12 types among the 23 types of compounds are shown).
Figure 4B:
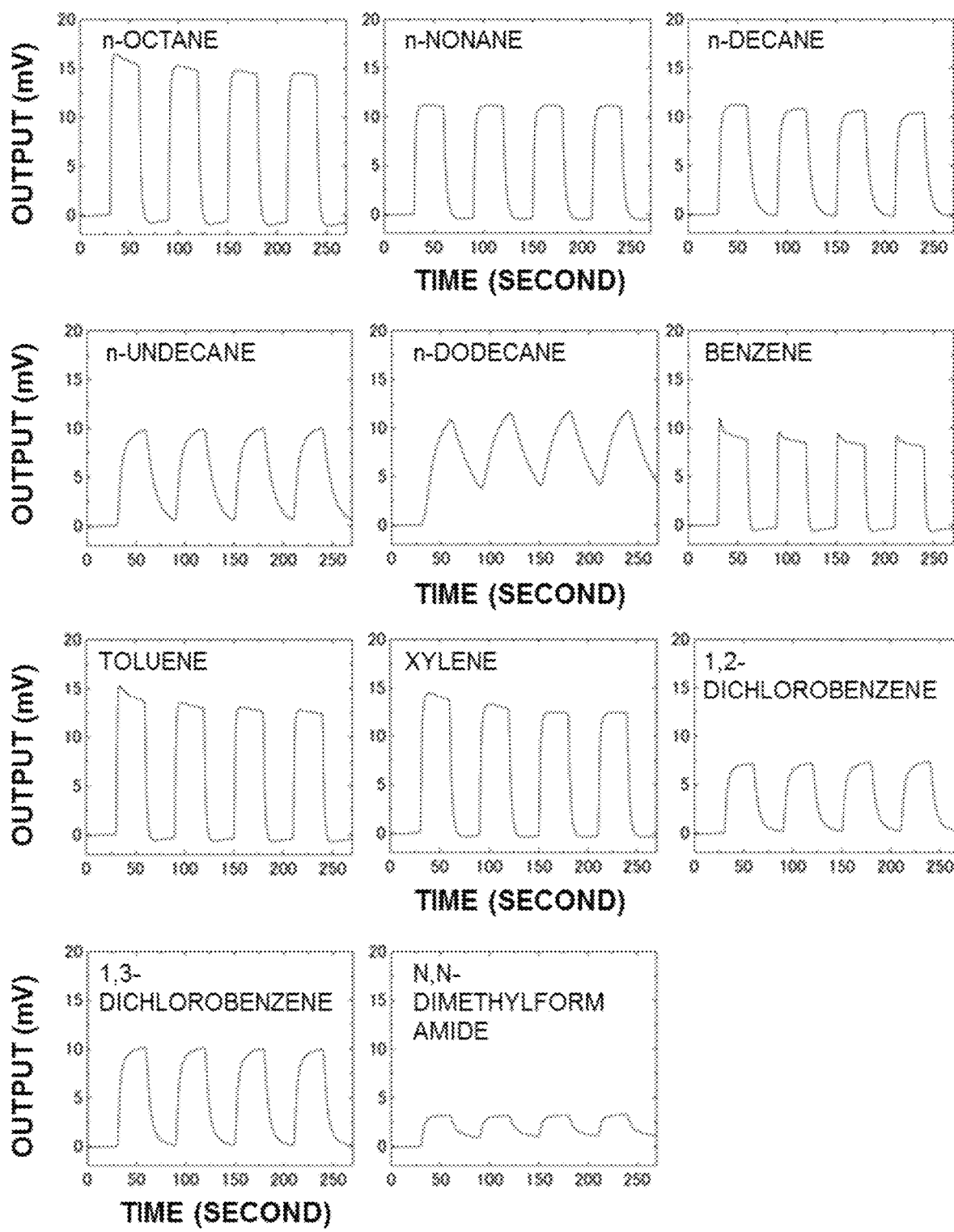
FIG. 4B shows results of measurements of 23 types of compounds by using an octadecyl group-modified nanoparticles-coated membrane-type surface stress sensor (results with respect to 11 types among the 23 types of compound are shown).
Figure 5:
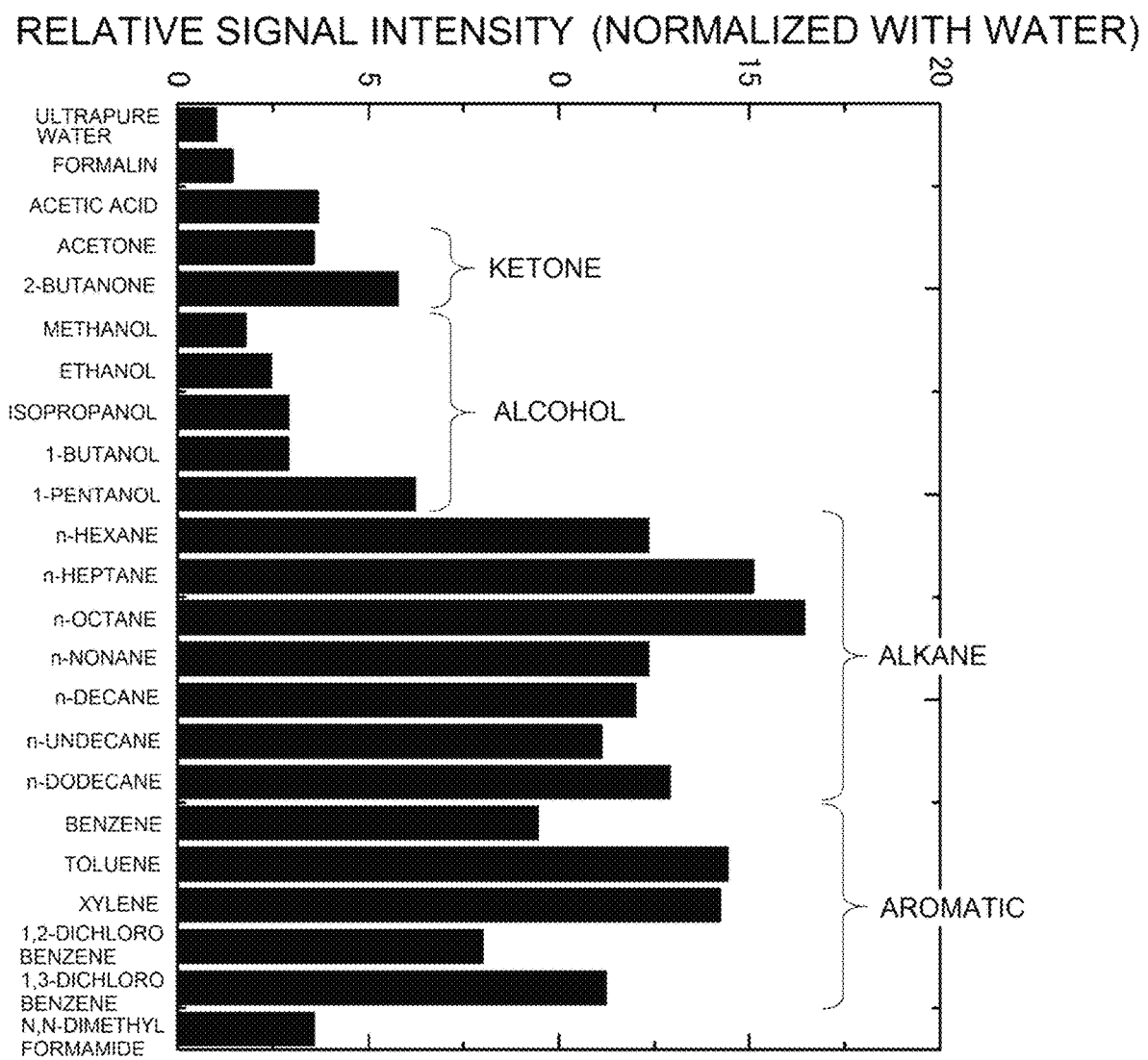
FIG. 5 shows relative signal intensities in which signal intensities with respect to vapors of samples are divided by a signal intensity with respect to water vapor shown in FIG. 4A and FIG. 4B.

Results of the measurements of the sample vapors are shown in FIG. 4A and FIG. 4B. Further, relative signal intensities in which signal intensities with respect to the sample vapors are divided by a signal intensity with respect to water vapor are shown in FIG. 5. Responses with respect to compounds which are slightly soluble in water are larger than responses with respect to water soluble compounds. The findings can be explained by the fact that an octadecyl group is a hydrophobic functional group.

Example 2

Figure 6:
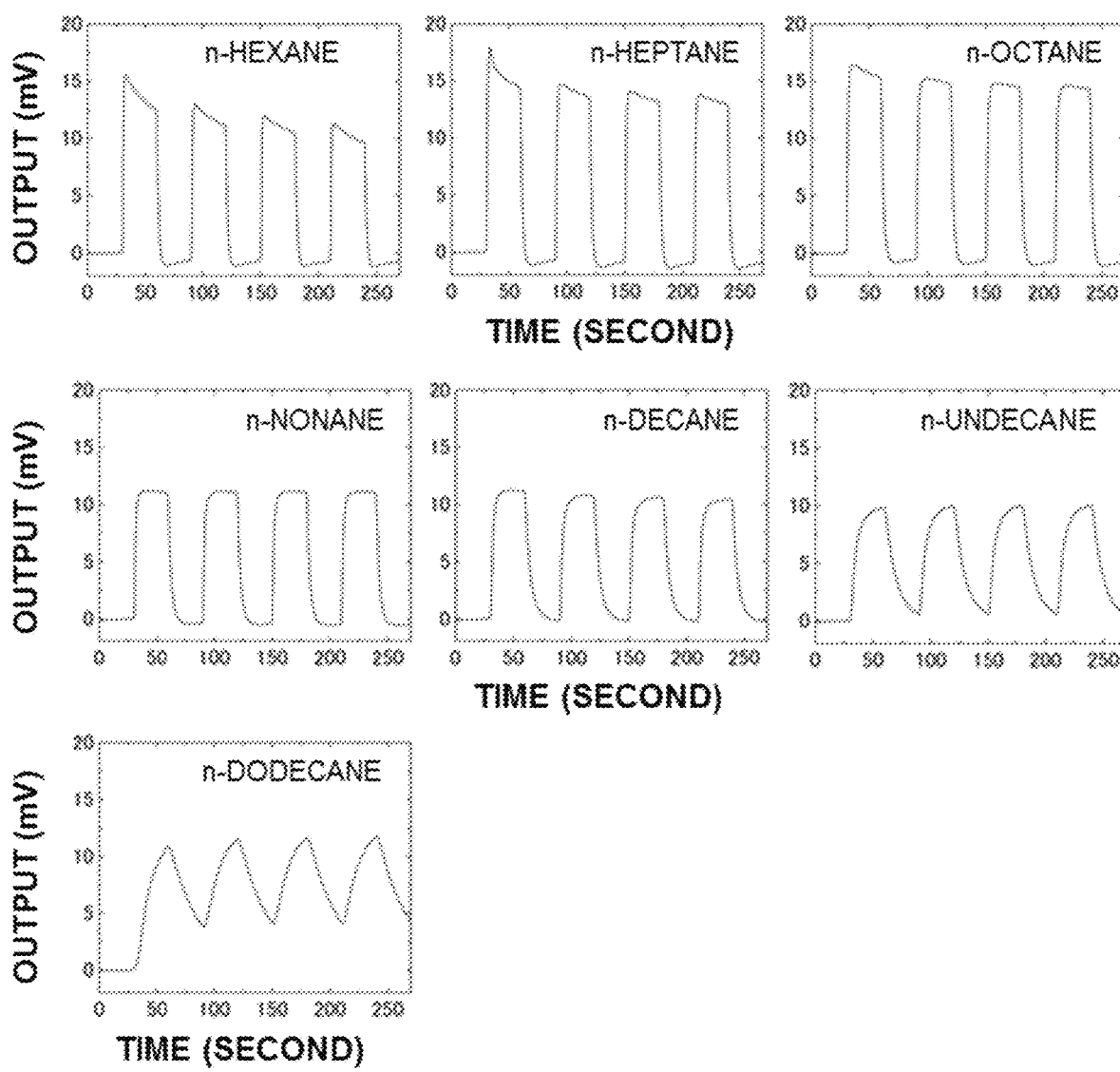
FIG. 6 shows results of measurements of seven types of alkanes by using an octadecyl group-modified nanoparticles-coated membrane-type surface stress sensor.

An alkane identification capability of a surface stress sensor coated with octadecyl group-modified silica-titania hybrid nanoparticles Next, capability of identification of a normal alkane molecule from other normal alkane molecules having very close chemical structures was studied by utilizing hydrophobic properties of the surface stress sensors coated with octadecyl group-modified silica-titania hybrid nanoparticles. As normal alkanes, seven types of alkanes having 6 to 12 carbon atoms were used. Here, results of the measurements are shown in FIG. 6. Sample vapors were obtained also at room temperature. It is found that each of the samples produced clearly different responses with respect to rising, intensity, and decay of signals. The difference is thought to reflect strengths of hydrophobic interactions between the normal alkane molecules, which were measured, and the octadecyl group which were stronger when lengths of alkyl chains constituting the alkane molecules were longer. With respect to decay part of the signals, longer alkyl chain length tends to result in decreased slope. The decreased slope means that the desorption of the alkane from the octadecyl group takes much time, supporting the above-described discussion.

Figure 7A:
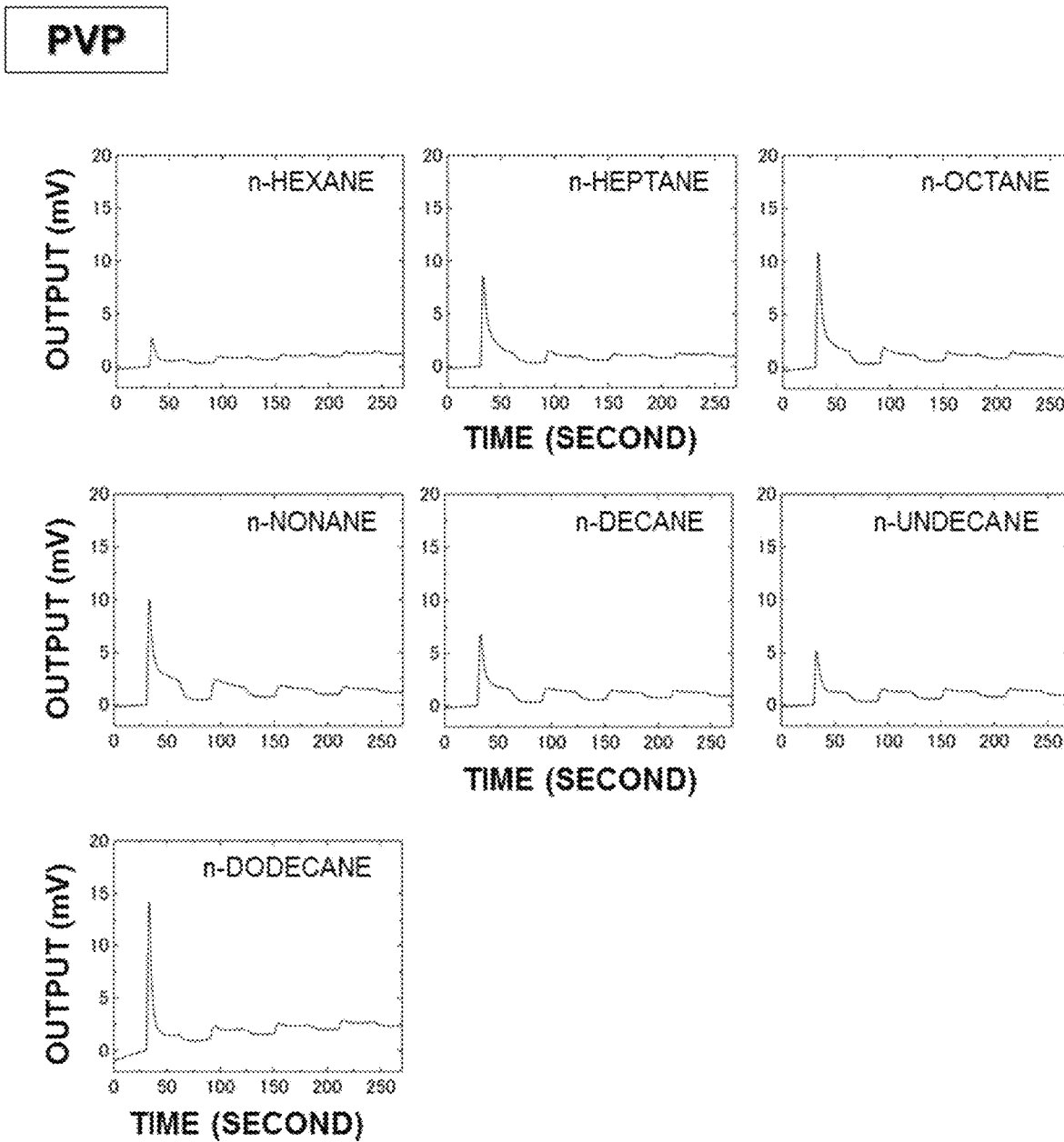
FIG. 7A shows results of measurements of seven types of alkanes by using PVP-coated membrane-type surface stress sensor.
Figure 7B:
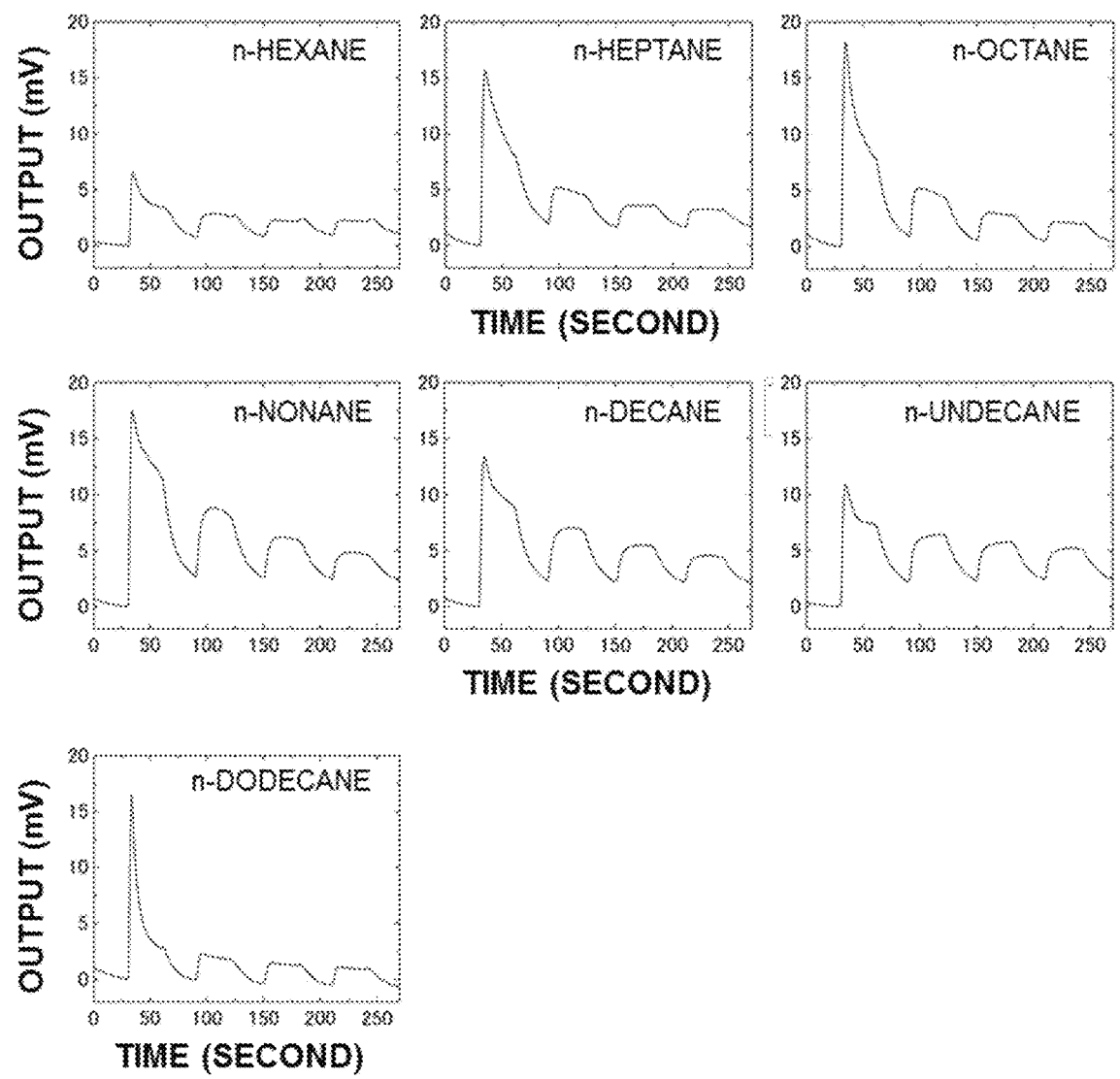
FIG. 7B shows results of measurements of seven types of alkanes by using PAA-coated membrane-type surface stress sensor.
Figure 7C:
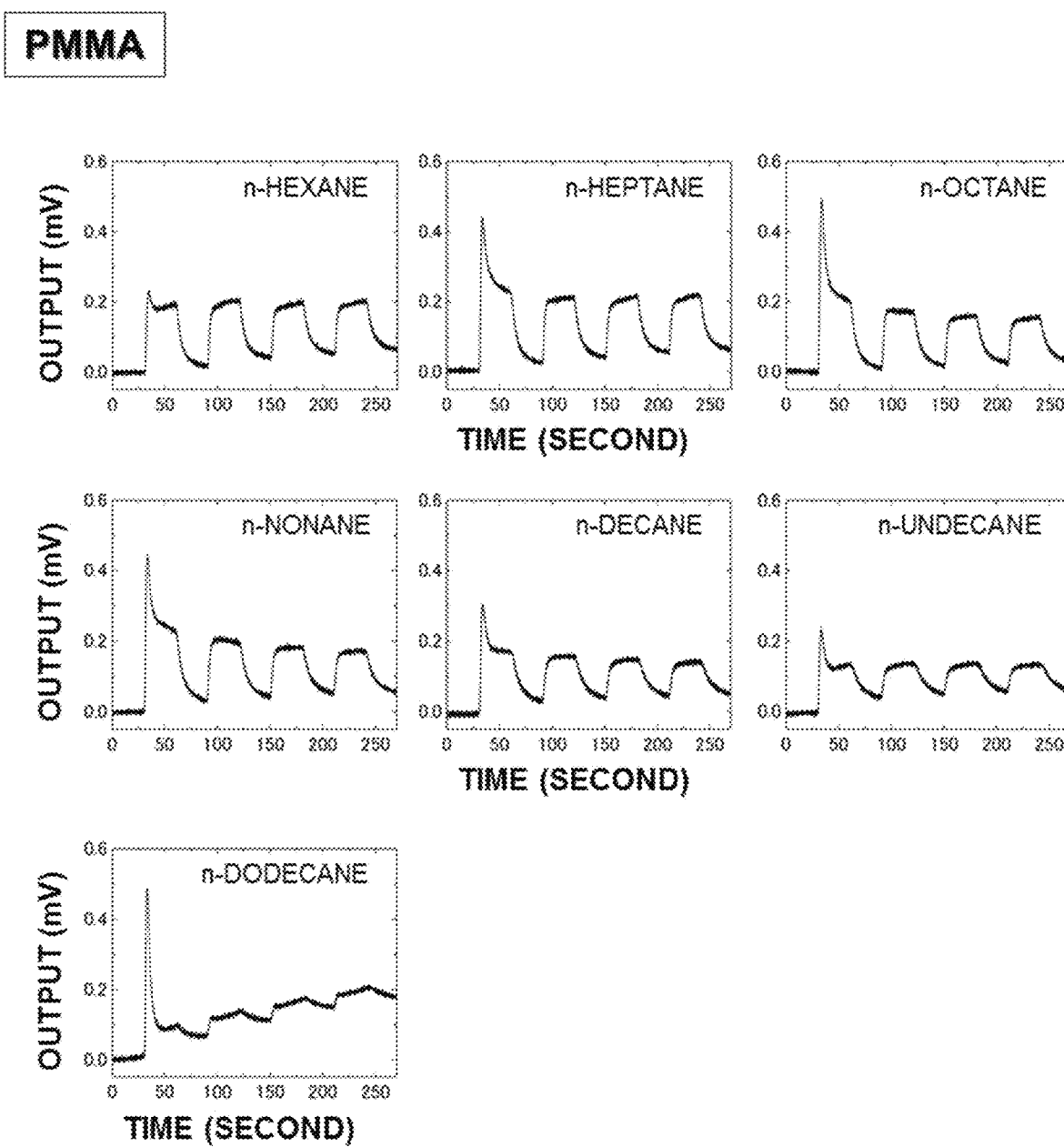
FIG. 7C shows results of measurements of seven types of alkanes by using PMMA-coated membrane-type surface stress sensor.

As comparative examples, three types of commercially available polymers (polyvinyl pyrrolidone: PVP, polyallylamine: PAA, and polymethyl methacrylate: PMMA) were used to perform measurements in a similar manner. Results of the measurements are shown in FIG. 7A to FIG. 7C. With respect to PVP and PAA, shapes of signals are changed with repeated measurements, and it is proved to be difficult to obtain consistent results. On the other hand, with respect to PMMA, although shapes of signals are relatively uniform, intensity is several tens of times smaller than that obtained by using octadecyl group-modified nanoparticles, and it is found to be inferior in detection sensitivity. Consequently, it was demonstrated that various alkanes can be measured with high sensitivity and high reproducibility by using octadecyl group-modified nanoparticles.

Figure 8:
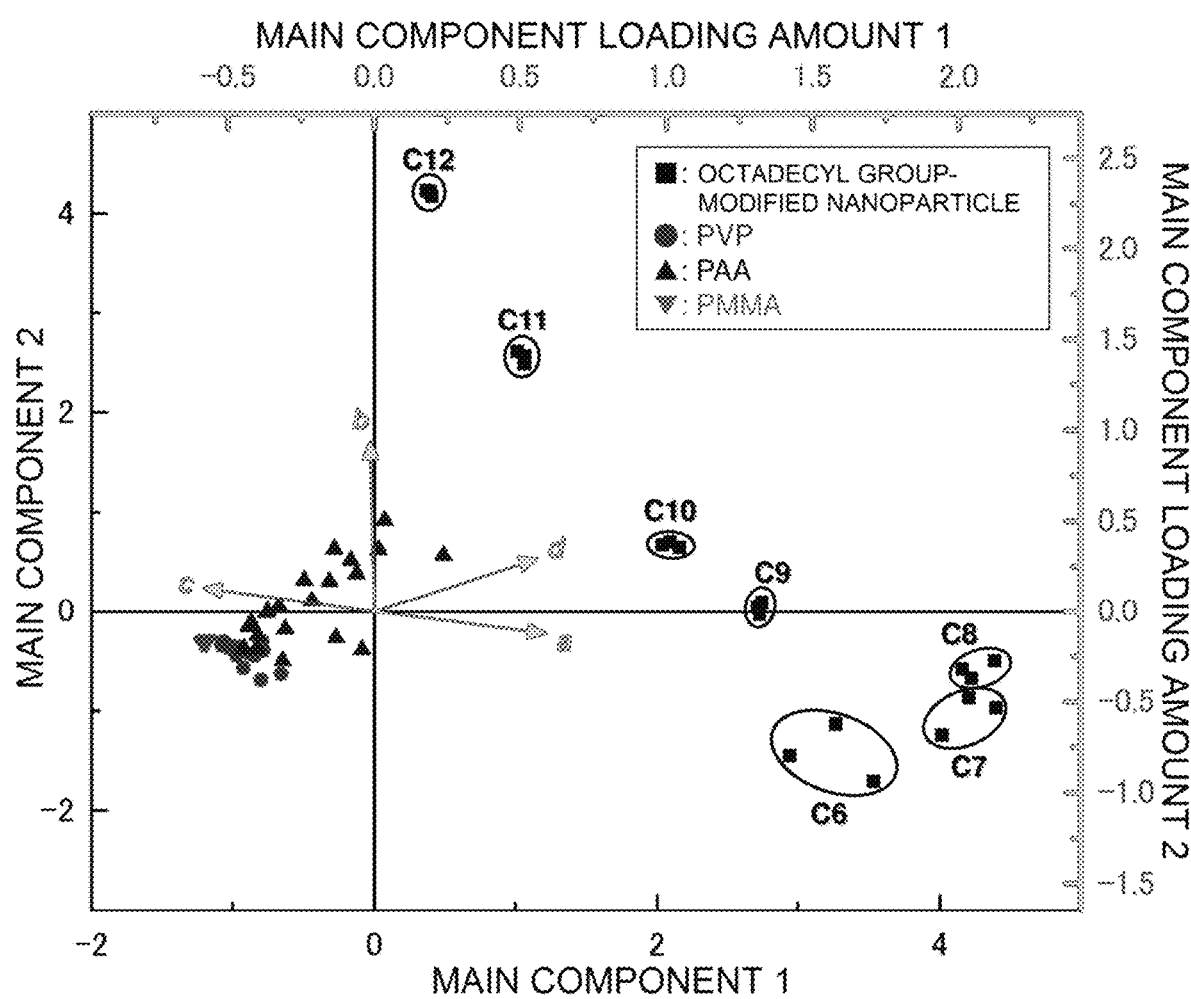
FIG. 8 shows results of principal component analysis on the basis of the results of the measurements of seven types of alkanes by using octadecyl group-modified nanoparticles-, PVP-, PAA-, and PMMA-coated membrane-type surface stress sensors.
Figure 9A:
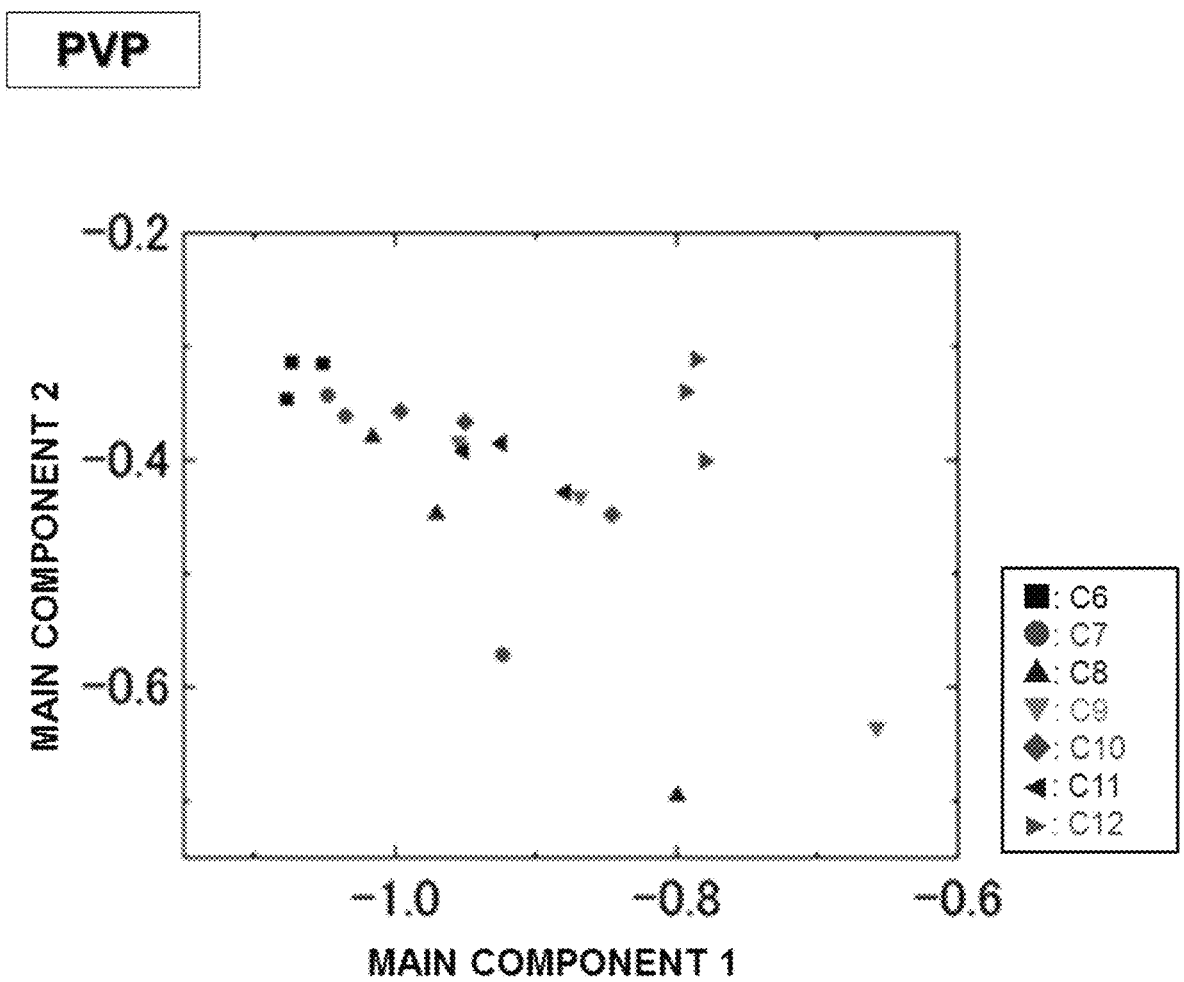
FIG. 9A is a magnified view of a PVP part in FIG. 8.
Figure 9B:
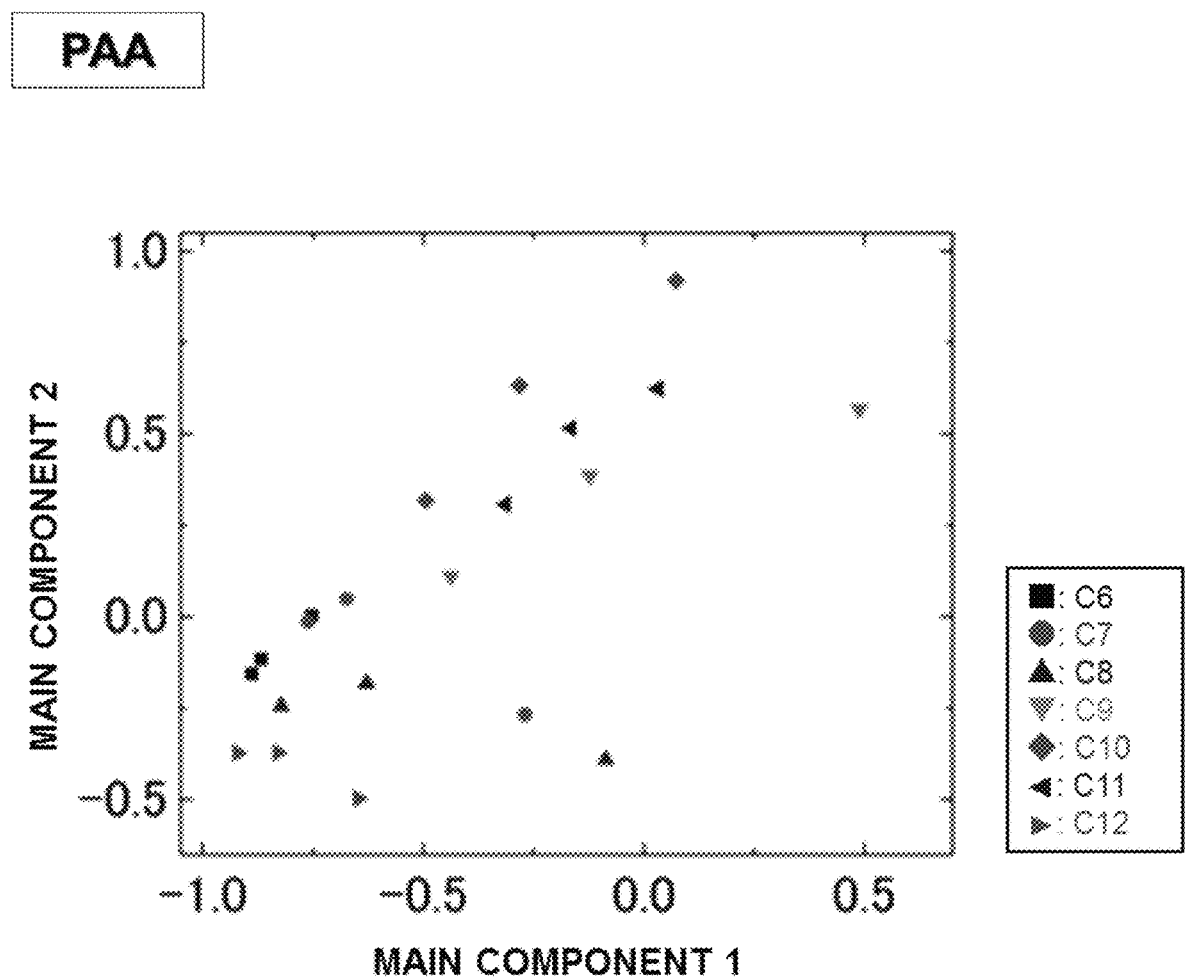
FIG. 9B is a magnified view of a PAA part in FIG. 8.
Figure 9C:
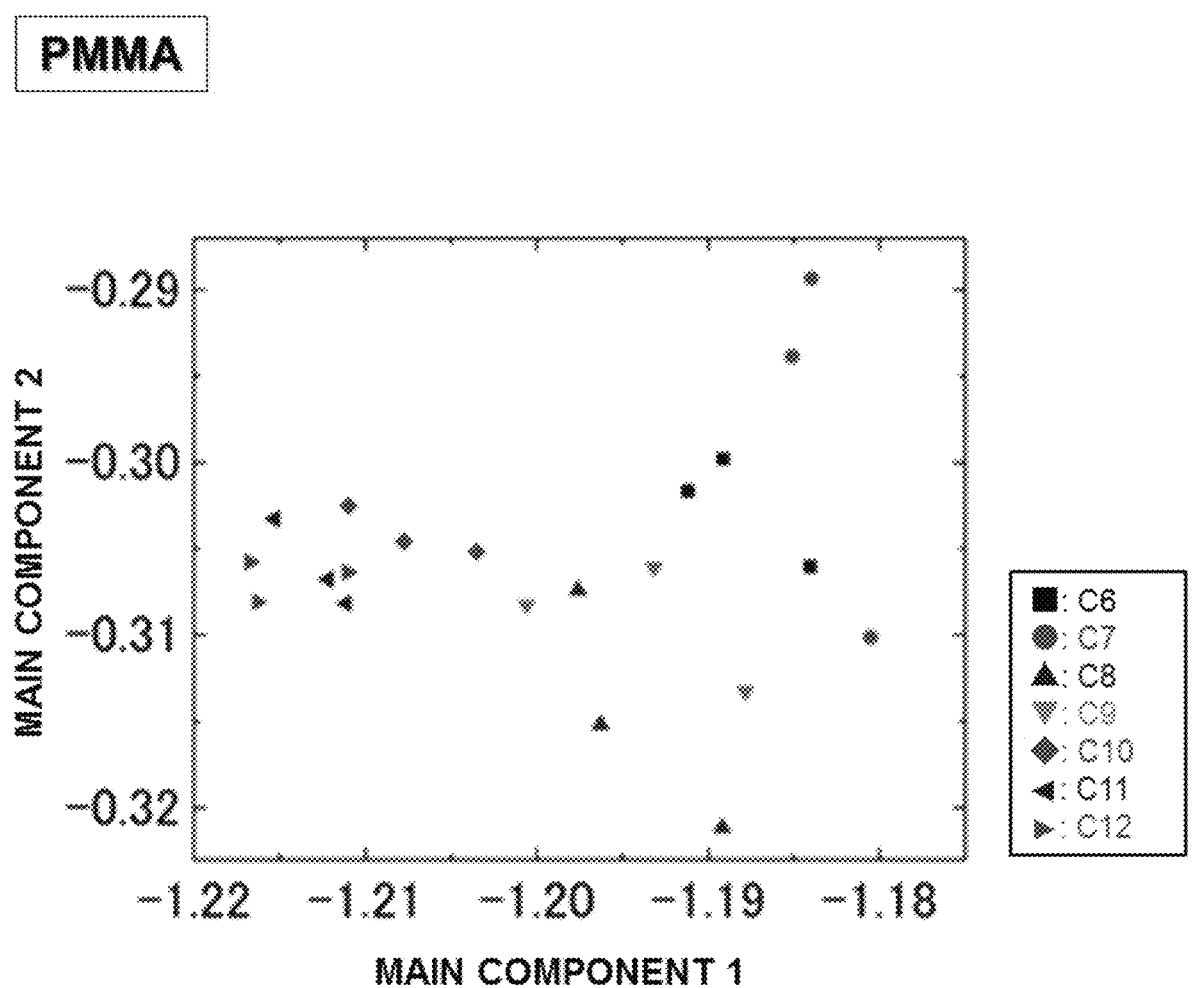
FIG. 9C is a magnified view of a PMMA part in FIG. 8.

For quantitative interpretation of the above-described results of the measurements, principal component analysis was performed. Specifically, on the basis of results obtained from the measurements of seven types of alkanes by using octadecyl group-modified nanoparticles and three types of polymers, a slope of rising (0 to 5 seconds), a slope of midway (5 to 30 seconds), a slope of decay (30 to 35 seconds), and intensity at 5 seconds after the rising were extracted, and four-dimensional data sets were produced. From the results, four-dimensional mapping was performed, and a two-dimensional projection chart shown in FIG. 8 was obtained. Since parameters having different properties were used, all data were standardized in advance, and correlation matrix was used for calculation. Note that Origin 2015 from Lightstone Corp. was used as a software for the principal component analysis. When the octadecyl group-modified nanoparticles were used, the seven types of normal alkanes (the alkanes were identified by numbers of carbon atoms of each alkane appended to "C" in FIG. 8) were separated, and the results revealed that the alkanes can be identified. On the other hand, when the three types of polymers were used, principal component plots of the alkanes are clustered in small area, and identification is difficult. Magnified views of the areas around the plots with respect to the three types of polymers in FIG. 8 are shown in FIG. 9A to FIG. 9C, respectively. From the figures, it is also difficult to say that the seven types of the alkanes are separated with a certain tendency when measurements were performed by using the polymers, and thus it was demonstrated that the alkanes were hard to be identified.

Example 3

A fuel oil identification capability of a surface stress sensor coated with octadecyl group-modified silica-titania hybrid nanoparticles Measurements of four types of fuel oils were performed according to the method described in Example 1. Specifically, commercially available regular gasoline and high-octane gas, diesel oil which is commercially available as a fuel for diesel engine automobiles, and heating oil were used. Here, sample vapors were obtained also at room temperature. As receptor materials, the three types of polymers described in Example 2 were also used in addition to octadecyl group-modified silica-titania hybrid nanoparticles. Results of the measurements are shown in FIG. 10, and FIG. 11A to FIG. 11C. When the octadecyl group-modified nanoparticles were used, it is found that each of the samples produced clearly different response with respect to rising, intensity, and decay of signals similarly to the measurements of seven types of normal alkanes described in Example 2. Similarly, when the three types of polymers were used, shapes of signals are changed with repeated measurements with respect to PVP and PAA, and it is proved to be difficult to obtain consistent results. On the other hand, with respect to PMMA, although shapes of signals are relatively uniform, intensity is several tens of times smaller than that obtained by using octadecyl group-modified nanoparticles, and it is found to be inferior in detection sensitivity.

Figure 10:
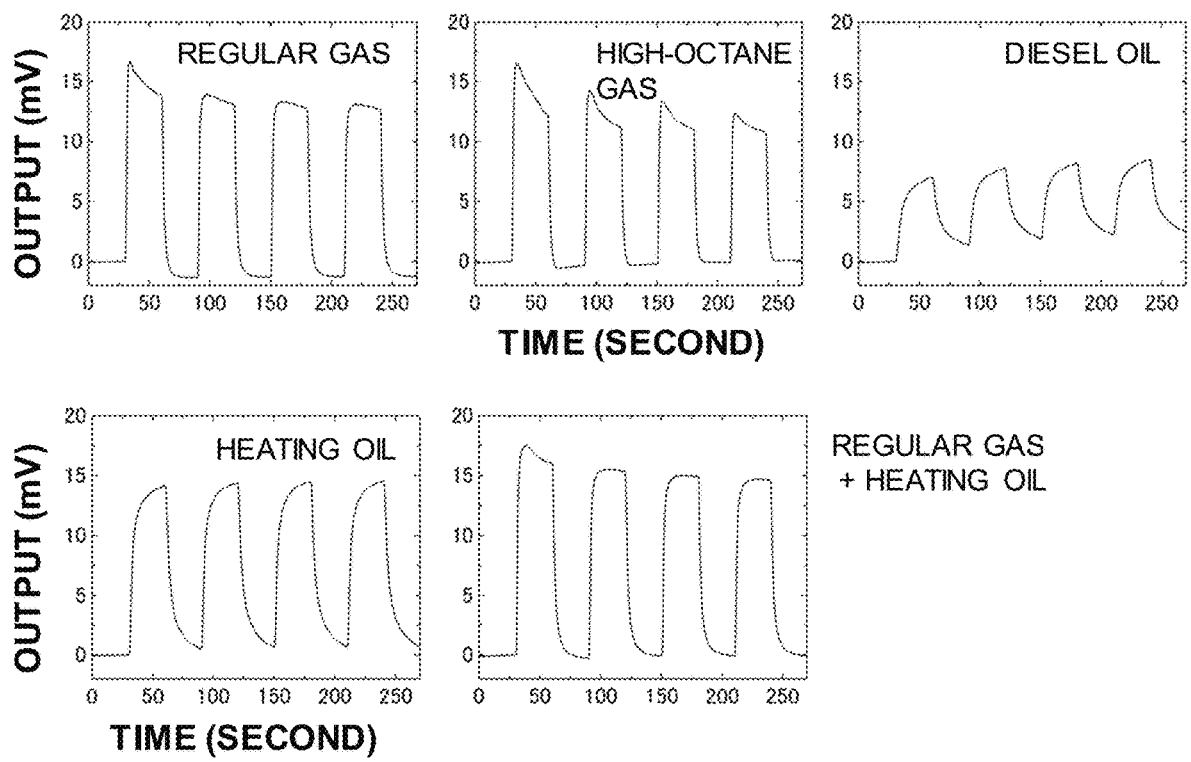
FIG. 10 shows results of measurements of regular gasoline, high-octane gasoline, diesel oil, heating oil, and regular gasoline mixed with heating oil by using an octadecyl group-modified nanoparticles-coated membrane-type surface stress sensor.
Figure 11A:
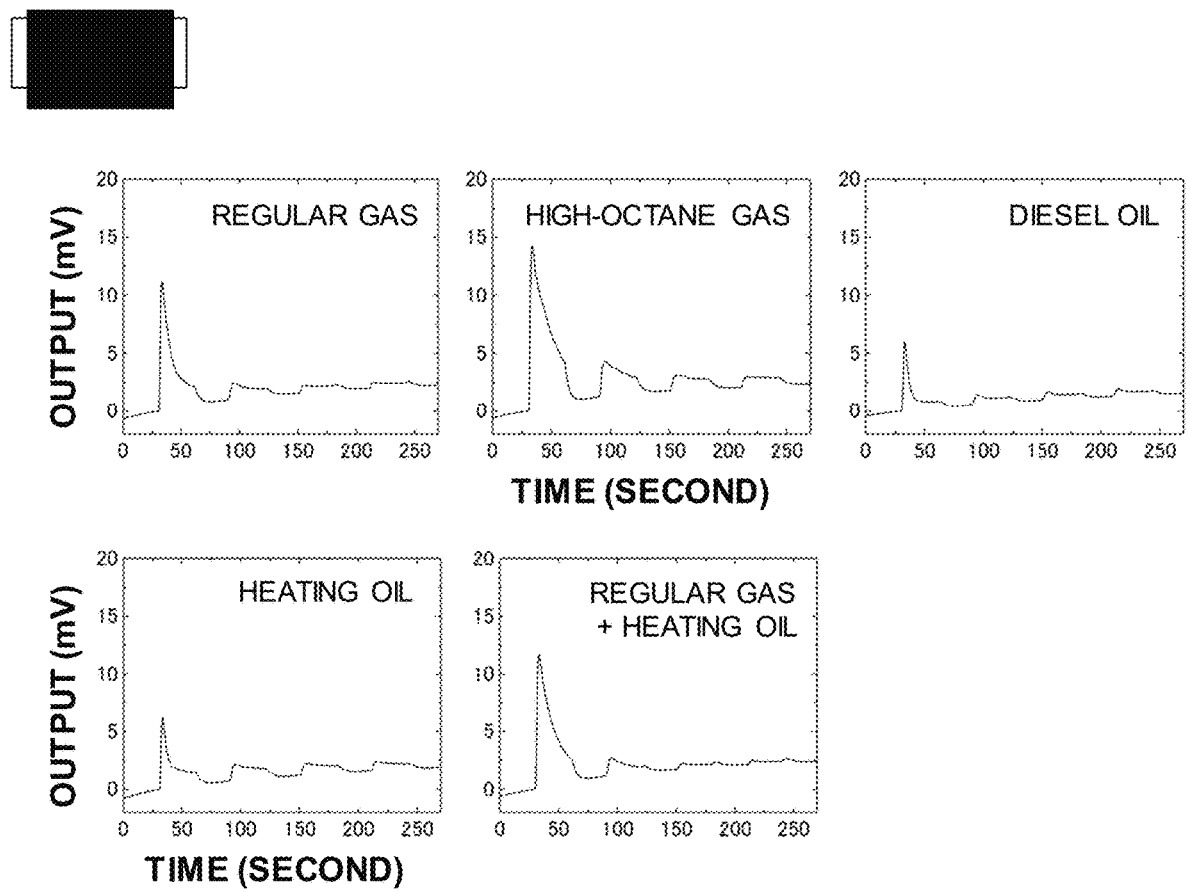
FIG. 11A shows results of measurements of regular gasoline high-octane gasoline, diesel oil, heating oil, and a mixture of regular gasoline and heating oil by using a PVP-coated membrane-type surface stress sensor.
Figure 11B:
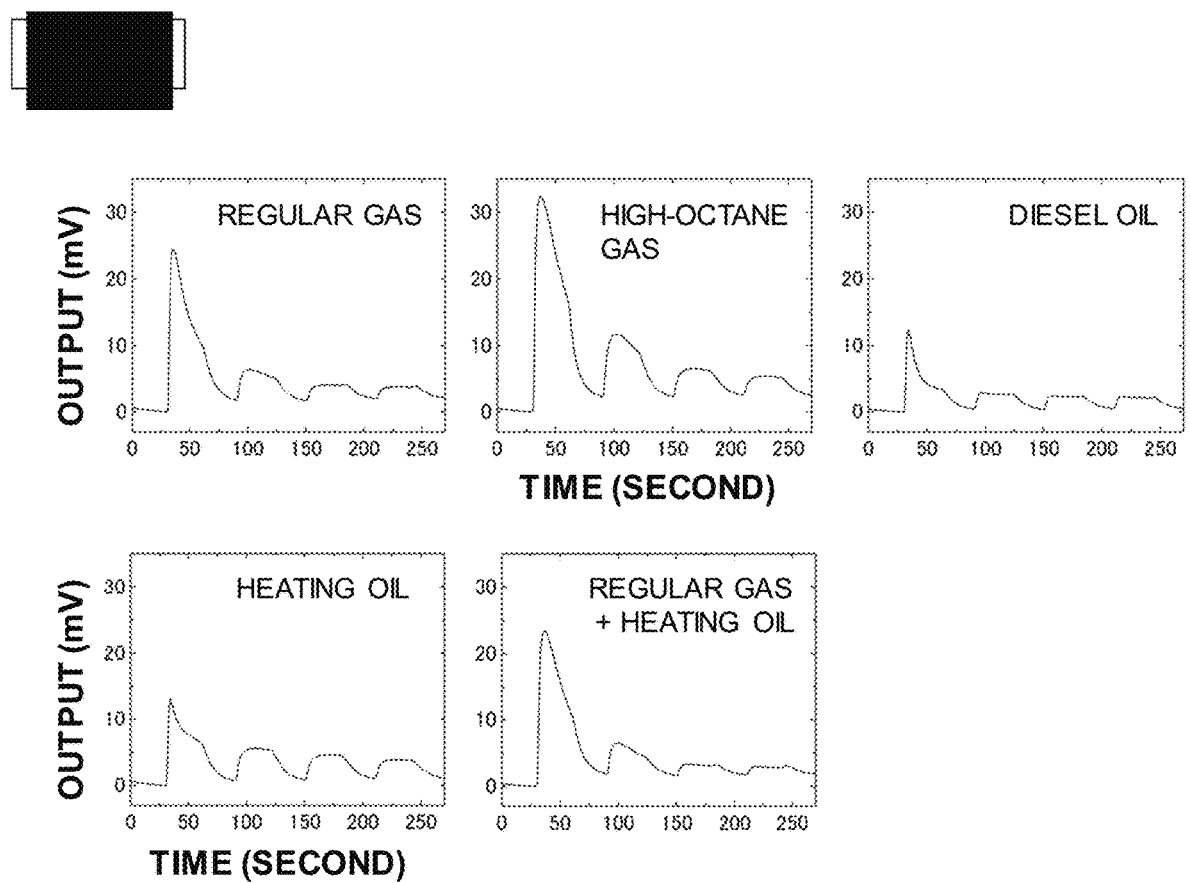
FIG. 11B shows results of measurements of regular gasoline, high-octane gasoline, diesel oil, heating oil, and a mixture of regular gasoline and heating oil by using a PAA-coated membrane-type surface stress sensor.
Figure 11C:
FIG. 11C shows results of measurements of regular gasoline, high-octane gasoline, diesel oil, heating oil, and a mixture of regular gasoline and heating oil by using a PMMA-coated membrane-type surface stress sensor.
Figure 11C:
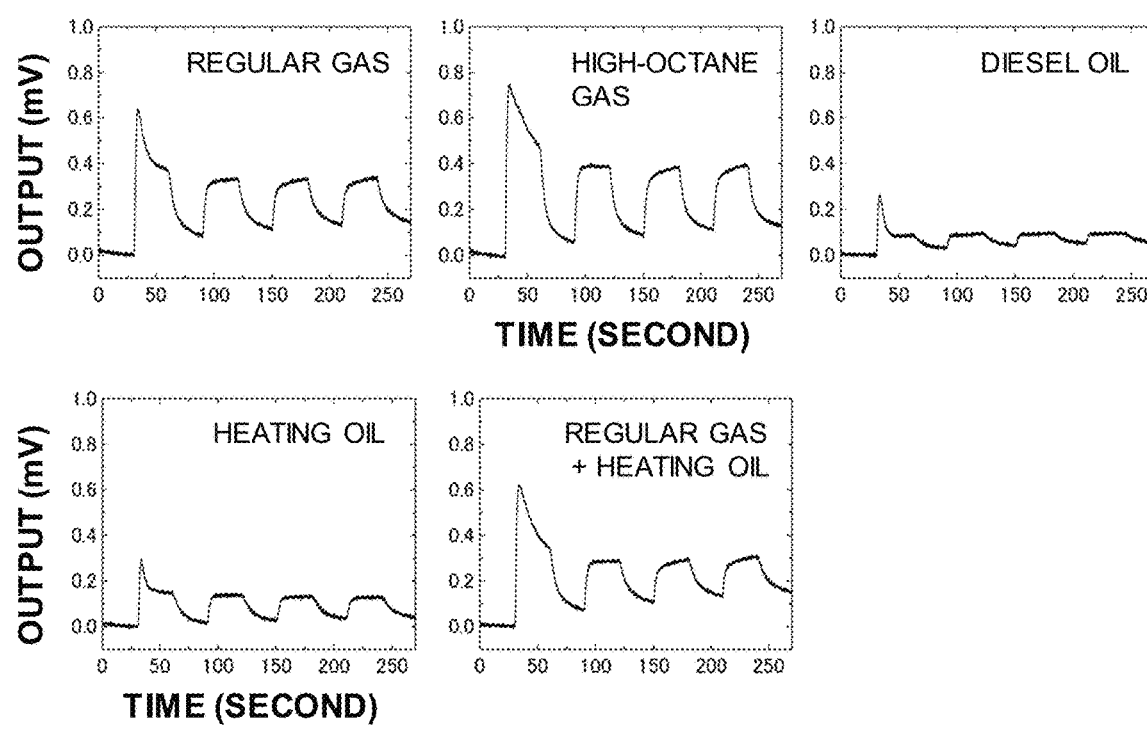
Figure 12:
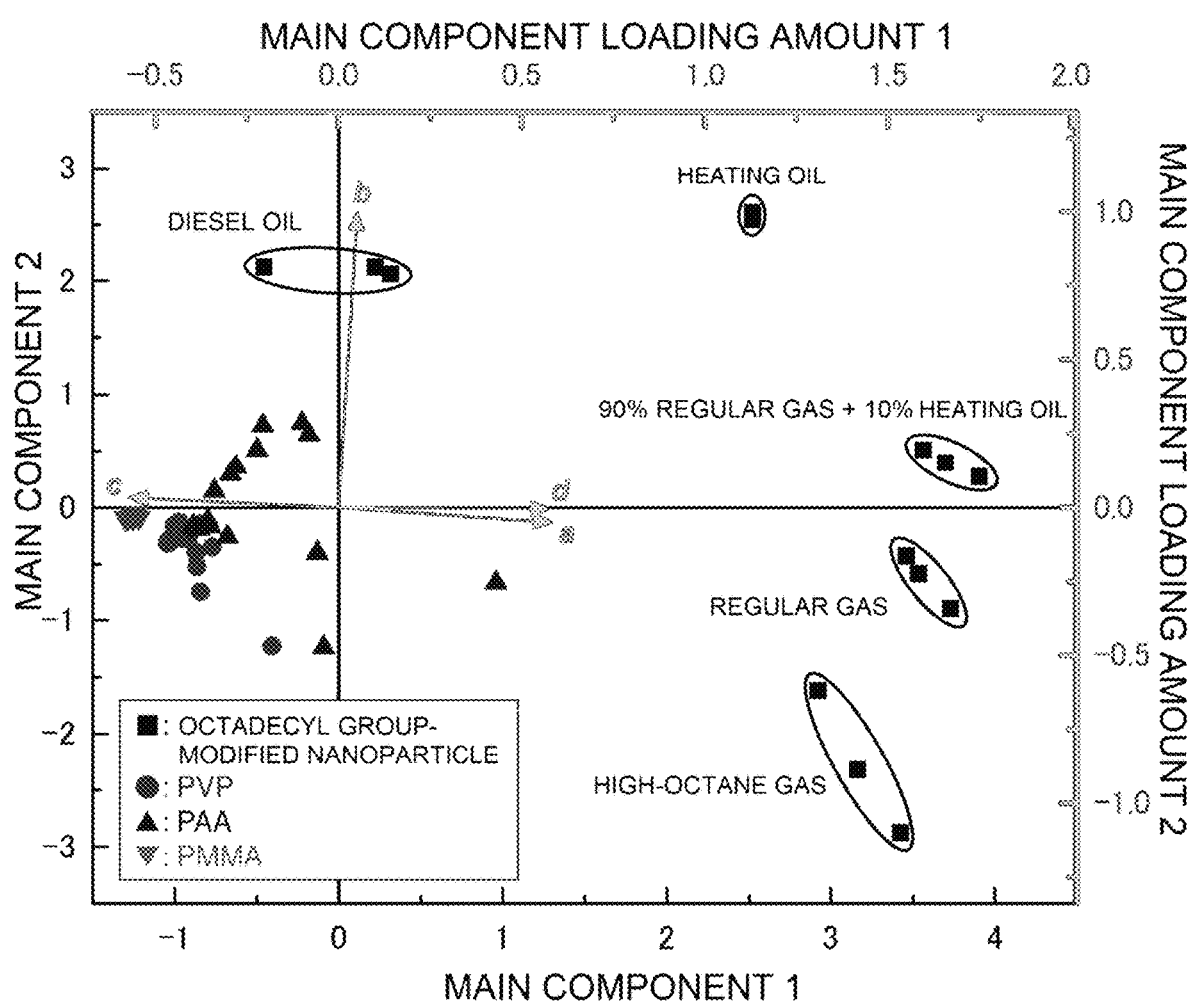
FIG. 12 shows results of principal component analysis on the basis of the results of the measurements of regular gasoline, high-octane gasoline, diesel oil, heating oil, and regular gasoline mixed with heating oil by using an octadecyl group-modified nanoparticles-, PVP-, PAA-, and PMMA-coated membrane-type surface stress sensor.
Figure 13A:
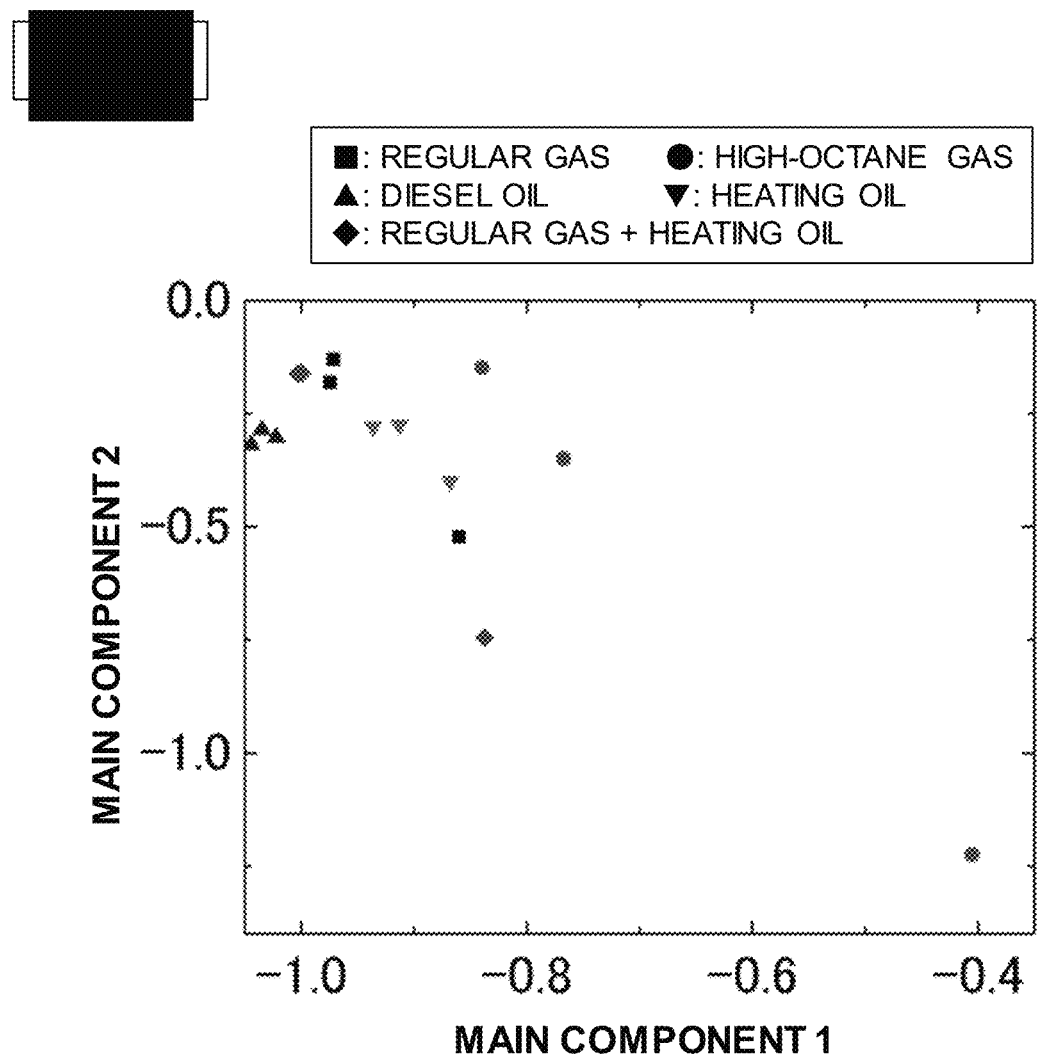
FIG. 13A is a magnified view of a PVP part in FIG. 12.
Figure 13B:
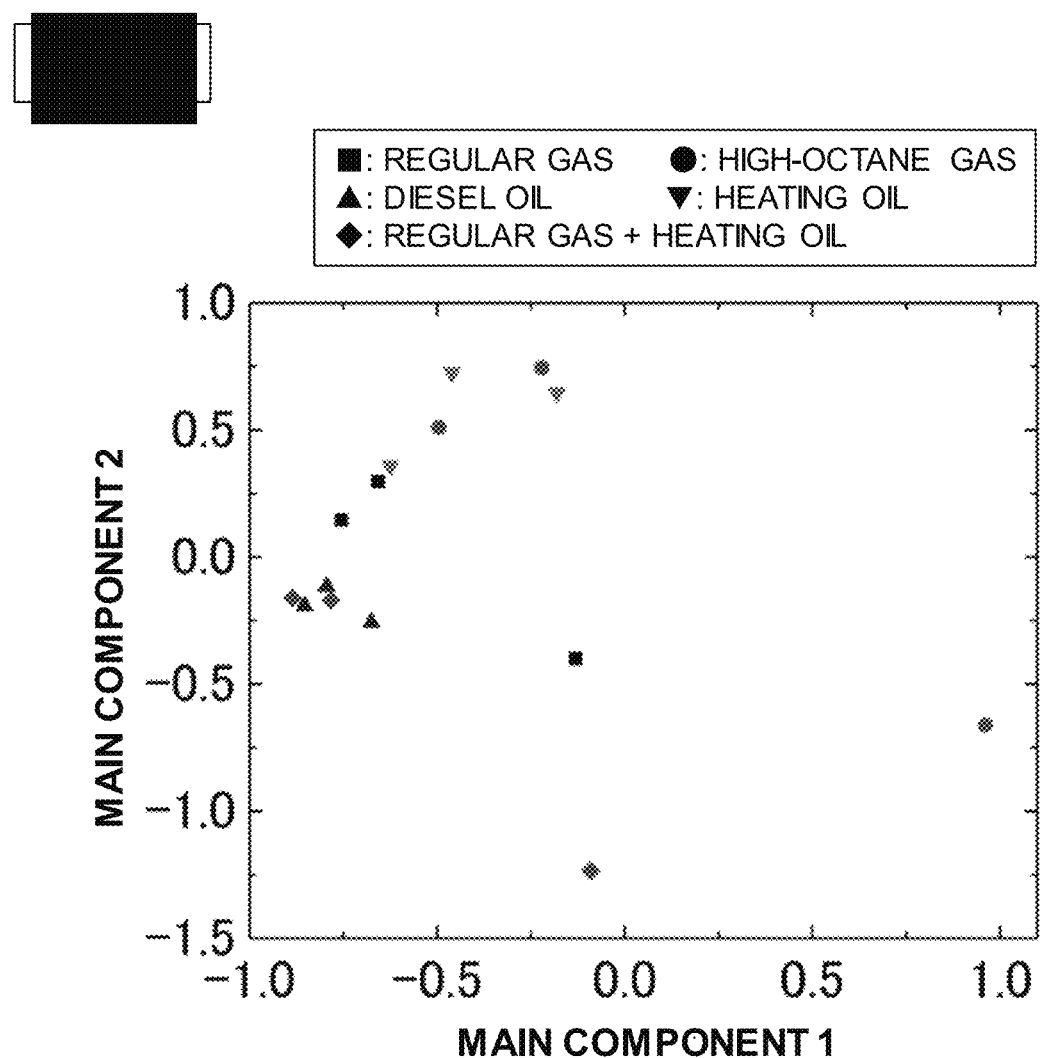
FIG. 13B is a magnified view of a PAA part in FIG. 12.
Figure 13C:
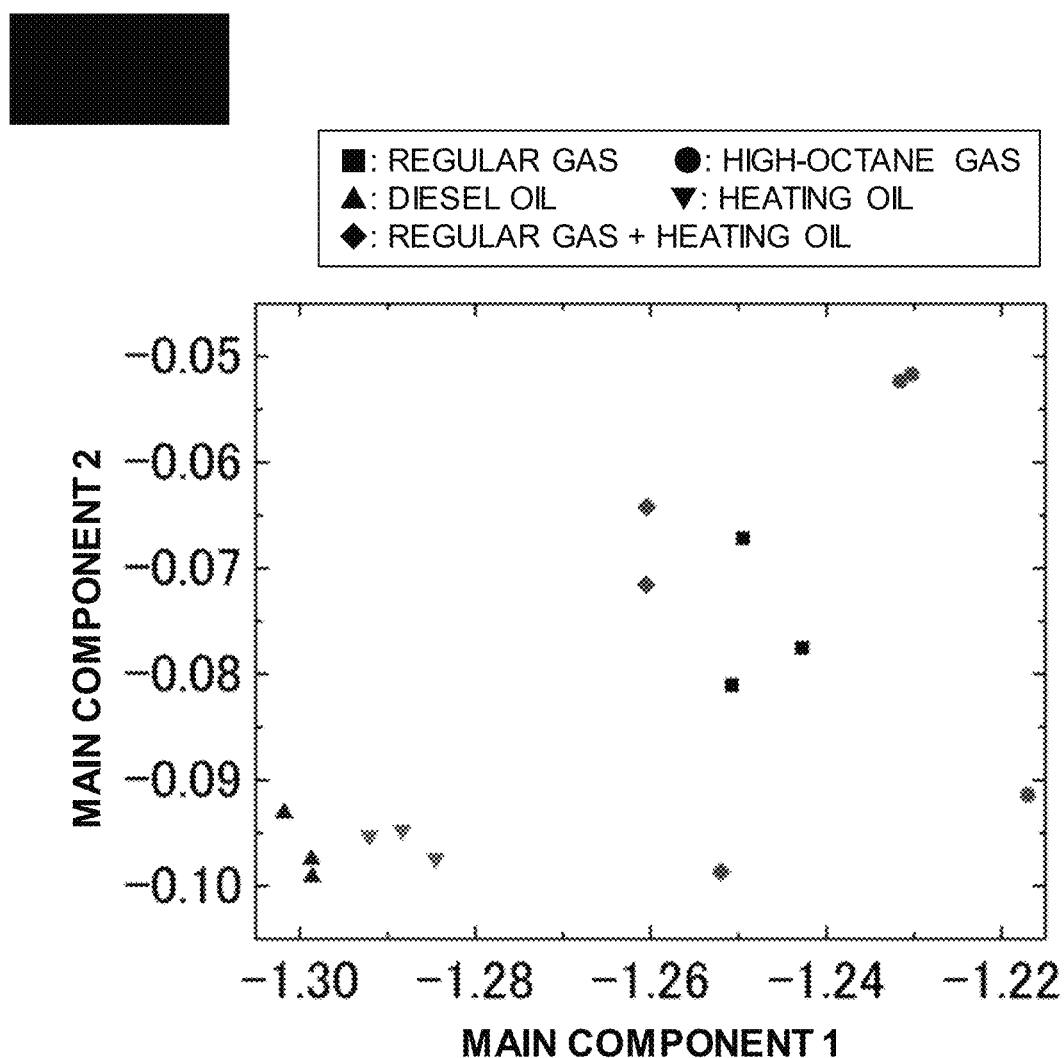
FIG. 13C is a magnified view of a PMMA part in FIG. 12.

Results of principal component analysis performed according to a method similar to the method described in Example 2 are shown in FIG. 12, and FIG. 13A to FIG. 13C. The results reveal that, when octadecyl group-modified nanoparticles were used, four types of fuel oils were separated, and the fuel oils can be identified, whereas identification of the fuel oils was difficult by using the three types of polymers. The reason for this can be explained on the basis of the fact that constituents of the four types of fuel oils are slightly different from each other. That is, it is known that diesel oil and heating oil contain a high percentage of long chain alkanes, whereas regular gas and high-octane gas contain a high percentage of volatile short chain alkanes. With respect to shapes of signals, results of measurements of regular gas and high-octane gas shown in FIG. 10 are similar to shapes with respect to n-hexane, n-heptane, and n-octane shown in FIG. 6, and results of measurements of diesel oil and heating oil shown in FIG. 10 are similar to shapes with respect to n-undecane and n-dodecane shown in FIG. 6.

An octadecyl group-modified nanoparticle of the present invention can identify difference in only one carbon atom in normal alkane molecules as shown also in Example 2. Accordingly, when a main component is several types of normal alkanes, and contents of the normal alkanes are different with one another as in fuel oils used in the present examples, highly accurate identification can be achieved by using only a single receptor. Further, as can be seen from FIG. 12, since diesel oil and heating oil can be clearly identified, an adulterated diesel oil using heating oil or heavy oil and a proper diesel oil can be identified.

Further, when regular gasoline was mixed with a small amount of heating oil in a volume ratio of 9:1 and the mixture was measured, results of the measurement were different from those with respect to regular gas and heating oil, and thus it was found that identification was possible by principal component analysis. This indicates that a sample of gasoline with alcohol or heating oil mixed in for the purpose of adding volume can easily be identified by using a single receptor.

Example 4

Figure 14A:
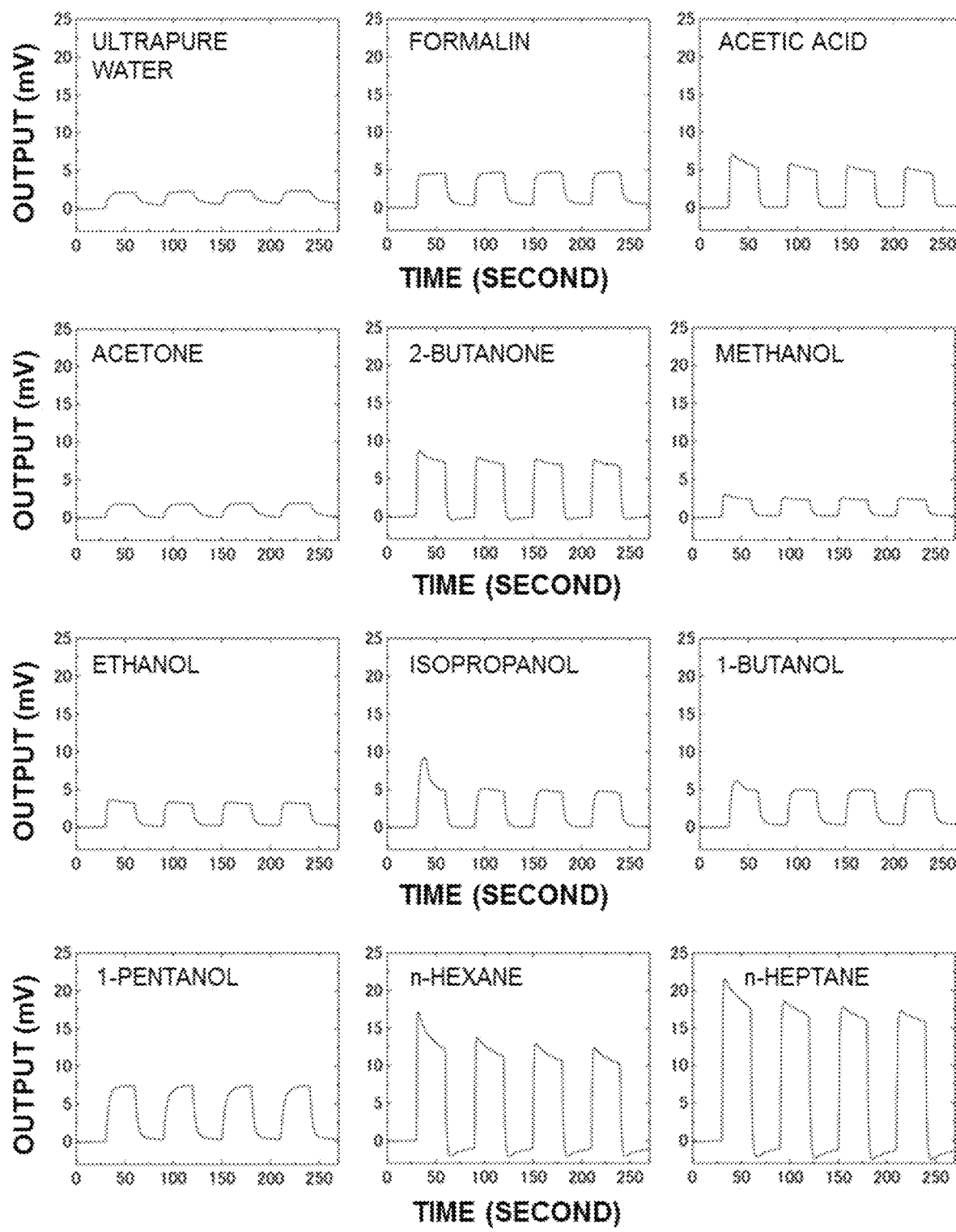
FIG. 14A shows results of measurements of 23 types of compounds by using a dodecyl group modified a nanoparticles-coated membrane-type surface stress sensor (results with respect to 12 types among the 23 types of compounds are shown).
Figure 14B:
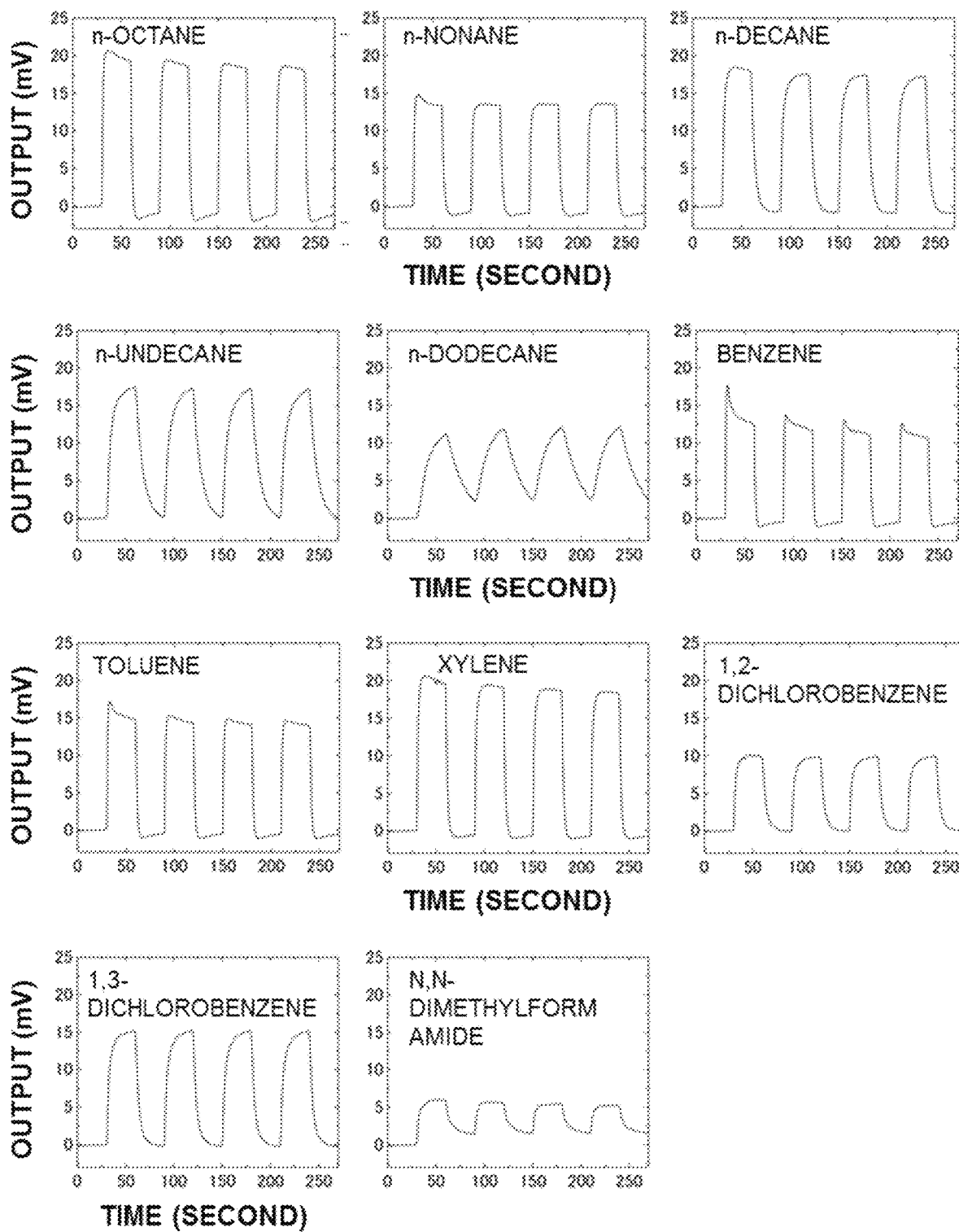
FIG. 14B shows results of measurements of 23 types of compounds by using a dodecyl group modified a nanoparticles-coated membrane-type surface stress sensor (results with respect to 11 types among the 23 types of compounds are shown).

A surface stress sensor coated with dodecyl group modified silica-titania hybrid nanoparticles Silica-titania hybrid nanoparticles modified with dodecyl groups were synthesized according to the method described in Example 1. The only difference in the synthesis procedures is that dodecyltriethoxysilane (DDTES) was used instead of ODTES. Then, dispersions were prepared according to the method described in Example 1, and a surface of a sensor was coated by spray coating. Then, measurements of 23 types of chemical species described in Example 1 were performed. Here, sample vapors were obtained also at room temperature. Results of the measurements are shown in FIG. 14A and FIG. 14B.

Figure 15:
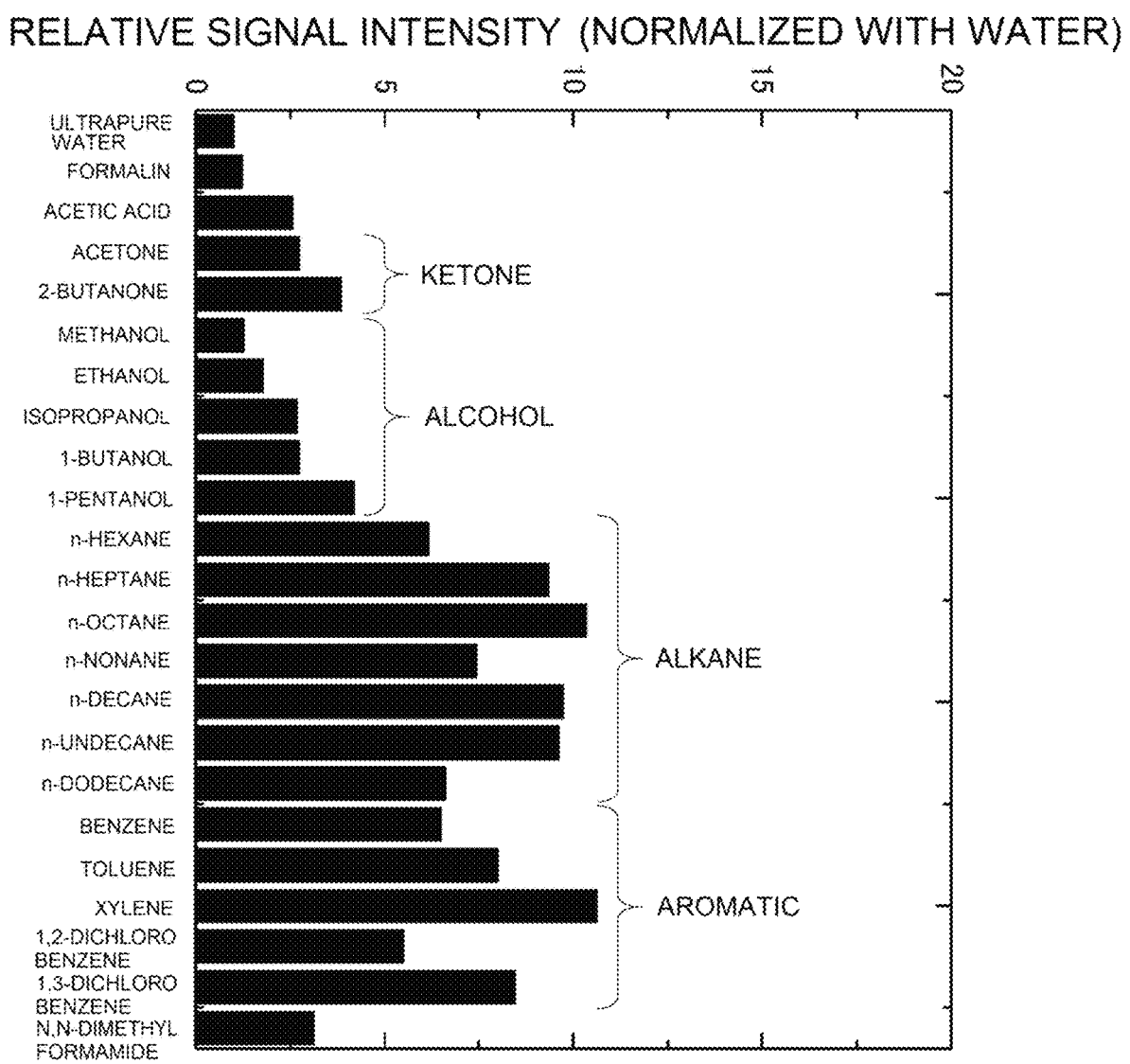
FIG. 15 shows relative signal intensities in which signal intensities with respect to vapors of samples are divided by a signal intensity with respect to water vapor in FIG. 14A and FIG. 14B.

Further, relative signal intensities in which signal intensities with respect to sample vapors are divided by a signal intensity with respect to water vapor are shown in FIG. 15. Tendencies of the signal intensities are almost similar to those with respect to octadecyl group-modified nanoparticles, and responses with respect to compounds which are slightly soluble in water are larger than responses with respect to water soluble compounds. However, ratios of signal intensities obtained by measurements of the compounds which are slightly soluble in water to signal intensities obtained by measurements of the water soluble compounds are lower than ratios obtained by using octadecyl group-modified nanoparticles. The reduced ratios are thought to reflect smaller hydrophobicity by using a dodecyl group having fewer carbon atoms than those of an octadecyl group. In view of the fact that alcohol and the like is used for the purpose of increasing volume, even a single receptor can exhibit a high ability of identifying fuel oils by using nanoparticles modified with an octadecyl group, which has a large numbers of carbon atoms.

INDUSTRIAL APPLICABILITY

As described above, commonly used hydrocarbons such as fuel oils can easily be identified according to the present invention. Accordingly, without limitation, when the present invention is applied to, for example, a fuel supply system of an internal combustion engine, a fuel supplied by accident, a fuel oil deteriorated by long-term storage, and a fraudulent fuel oil (e.g., gasoline, diesel oil), which can cause damage to an internal combustion engine or adjunct devices of the engine, can easily be detected, and thus the present invention is expected to be widely applicable to industries.

CITATION LIST

Patent Literature

Patent Literature 1: WO 2011/148774

Non Patent Literature

Non Patent Literature 1: Huihui Guo, Xiangdong Chen, and Yao Yao, "A Room Temperature polymer-Coated Piezoresistive Silicon Bridge Gasoline Vapor Sensor," IEEE SENSORS JOURNAL, VOL. 12, NO. 5, 926-929, (2012).

Non Patent Literature 2: K. Shiba, T. Sugiyama, T. Takei, and G. Yoshikawa, "Controlled growth of silica-titania hybrid functional nanoparticles through a multistep microfluidic approach," Chem. Commun. 51, 15874-15857 (2015).

The invention claimed is:
1. A fuel oil identification sensor for distinguishing and identifying at least one fuel oil from among a plurality of fuel oils comprising:
   a surface stress sensor and a receptor layer for fuel oil identification, wherein
   the surface stress sensor detects a change in a surface stress;
   the receptor layer comprises a particle of 1 mm or less in particle size and is modified with a hydrocarbon group;

a surface of the surface stress sensor is coated with the receptor layer; and the at least one fuel oil is distinguished and identified from among the plurality of fuel oils on the basis of the change in the surface stress.

2. The fuel oil identification sensor according to claim 1, wherein the particle is a nanoparticle having a particle size of 100 nm or less.

3. The fuel oil identification sensor according to claim 1, wherein the particle comprises at least one member selected from the group consisting of zeolite; a metal- organic framework; a hybrid of an oxide and/or a metal and various surfactants; a porous material; graphene; an alkali silicate or a titanate such as a clay mineral; and a low-dimensional compound comprising a transition metal oxoate.

4. The fuel oil identification sensor according to claim 1, wherein the receptor layer further comprises a matrix material other than the particle.

5. The fuel oil identification sensor according to claim 1, wherein the hydrocarbon group is an alkyl group or an aryl group.

6. The fuel oil identification sensor according to claim 5, wherein the alkyl group is an alkyl group having 1 to 30 carbon atoms.

7. The fuel oil identification sensor according to claim 6, wherein the alkyl group is a dodecyl group or an octadecyl group.

8. The fuel oil identification sensor according to claim 1, wherein the at least one fuel oil is distinguished and identified from among regular gasoline; high-octane gasoline; diesel oil; heating oil; a mixture of regular gasoline or high-octane gasoline with heating oil, a mixture of regular gasoline or high-octane gasoline with an alcohol; heavy oil A; a mixture of heavy oil A with heating oil; and/or a mixture of at least one of heavy oil A and heating oil with diesel oil.

9. A fuel oil identification method comprising:

supplying vapor of an analyte to the fuel oil identification sensor according to claim 1; and distinguishing and identifying the analyte on the basis of an output of the fuel oil identification sensor, wherein the analyte comprises at least one fuel oil from among the plurality of fuel oils.

10. The fuel oil identification method according to claim 9, wherein a mixture of the vapor of the analyte and another gas is supplied to the fuel oil identification sensor.

11. The fuel oil identification method according to claim 10, wherein the other gas is a gas or a mixture of a plurality of gases selected from the group consisting of nitrogen, air, argon, and helium.

12. The fuel oil identification method according to claim 9, wherein the vapor of the analyte is generated without heating or cooling.

13. The fuel oil identification method according to claim 9, wherein the vapor of the analyte is generated at room temperature.

14. The fuel oil identification method according to claim 9, comprising:

supplying the vapor of the analyte to a plurality of types of fuel oil identification sensors; and distinguishing and identifying the analyte on the basis of outputs of the respective fuel oil identification sensors.

15. The fuel oil identification method according to claim 9, wherein vapors of a plurality of analytes are switched in sequence for delivery to the fuel oil identification sensor.

16. The fuel oil identification method according to claim 15, wherein cleaning of the fuel oil identification sensor is not performed for at least one cycle of the switching for the delivery.

17. The fuel oil identification method according to claim 9, wherein identification of the analyte is made by further performing an information processing of the output of the fuel oil identification sensor.

18. The fuel oil identification method according to claim 17, wherein the information processing is based on at least one analytical method selected from the group consisting of principal component analysis, a neural network, deep learning, a support vector machine, random forest, a decision tree, regression analysis, and big data analysis.

* * * * *